United States Patent
Morita et al.

(10) Patent No.: US 9,696,253 B2
(45) Date of Patent: Jul. 4, 2017

(54) MICROCHIP AND FILM FORMING METHOD FOR METAL THIN FILM OF MICROCHIP

(71) Applicant: USHIO DENKI KABUSHIKI KAISHA, Tokyo (JP)

(72) Inventors: Kinichi Morita, Tokyo (JP); Toshikazu Kawaguchi, Sapporo (JP)

(73) Assignee: USHIO DENKI KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/895,405

(22) PCT Filed: Jun. 2, 2014

(86) PCT No.: PCT/JP2014/002911
§ 371 (c)(1),
(2) Date: Dec. 2, 2015

(87) PCT Pub. No.: WO2014/196185
PCT Pub. Date: Dec. 11, 2014

(65) Prior Publication Data
US 2016/0109356 A1    Apr. 21, 2016

(30) Foreign Application Priority Data

Jun. 4, 2013  (JP) .................. 2013-117836

(51) Int. Cl.
*B01L 3/00*  (2006.01)
*H01L 21/00* (2006.01)
(Continued)

(52) U.S. Cl.
CPC .......... *G01N 21/05* (2013.01); *C01G 23/053* (2013.01); *C03C 17/36* (2013.01);
(Continued)

(58) Field of Classification Search
CPC .................. B01L 3/00; H01L 21/00
(Continued)

(56) References Cited

U.S. PATENT DOCUMENTS

| | | | |
|---|---|---|---|
| 4,252,414 A * | 2/1981 | Kinugawa et al. | 349/132 |
| 6,406,921 B1 * | 6/2002 | Wagner et al. | 436/174 |
| 6,495,067 B1 * | 12/2002 | Ono | 252/299.61 |
| 6,682,942 B1 * | 1/2004 | Wagner et al. | 506/9 |
| 2003/0027327 A1 * | 2/2003 | Cunningham et al. | 435/287.2 |
| 2003/0138845 A1 * | 7/2003 | Li et al. | 435/7.1 |
| 2004/0086424 A1 * | 5/2004 | Schembri | 422/58 |
| 2005/0136685 A1 * | 6/2005 | Takenaka et al. | 438/778 |

(Continued)

FOREIGN PATENT DOCUMENTS

| JP | H06-167443 A | 6/1994 |
|---|---|---|
| JP | 2000-055805 A | 2/2000 |

(Continued)

OTHER PUBLICATIONS

International Search Report—PCT/JP2014/002911 dated Aug. 12, 2014.

*Primary Examiner* — Brian J Sines
(74) *Attorney, Agent, or Firm* — Studebaker & Brackett PC

(57) ABSTRACT

Disclosed herein are a microchip provided with a titanium oxide film between a glass substrate and a metal thin film; and a method for forming the metal thin film and the titanium oxide film on the glass substrate of the microchip. The microchip has a second microchip substrate that has the metal thin film inside a channel, and the titanium oxide film, which has a low extinction coefficient, is provided as a buffer layer between the substrate and the metal thin film such as a gold film.

2 Claims, 27 Drawing Sheets

(51) Int. Cl.
*G01N 21/05* (2006.01)
*C01G 23/053* (2006.01)
*C03C 17/36* (2006.01)

(52) U.S. Cl.
CPC ...... *C03C 17/3607* (2013.01); *C03C 17/3642* (2013.01); *C03C 17/3649* (2013.01); *C03C 17/3657* (2013.01); *C03C 2217/70* (2013.01); *C03C 2217/75* (2013.01); *C03C 2218/111* (2013.01); *C03C 2218/31* (2013.01); *G01N 2021/056* (2013.01)

(58) Field of Classification Search
USPC .... 422/502, 503; 438/22, 23, 584, 761, 782, 438/785
See application file for complete search history.

(56) References Cited

U.S. PATENT DOCUMENTS

2009/0161110 A1 6/2009 Lin et al.
2010/0159576 A1* 6/2010 Song et al. ................ 435/288.7

FOREIGN PATENT DOCUMENTS

| JP | 2001-262008 | A | 9/2001 |
| JP | 2002-257720 | A | 9/2002 |
| JP | 3714338 | B2 | 11/2005 |
| JP | 2006-187730 | A | 7/2006 |
| JP | 2014-162684 | A | 9/2014 |
| JP | 2014-235115 | A | 12/2014 |

* cited by examiner

[STEP4]

[STEP5]

[STEP6]

[GLASS SUBSTRATE]
(CLEAVED, HYDROXY GROUP TERMINATED)

[STEP1]

(c) GROWTH OF TITANIUM OXIDE FILM [(TITANIUM OXIDATION) → (BINDING OF TITANIUM AND OXYGEN) REPEATED]

(c-1) TITANIUM OXIDIZED WITH $NO_2^-$ (c-1) TITANIUM OXIDIZED WITH $NO_2^-$ (c-1) TITANIUM OXIDATION ($Ti^{3+}$ → $Ti^{4+}$)

[STEP1]

(c-2) BINDING OF TITANIUM AND OXYGEN FROM $H_2O$

[STEP1]

(c-3) BINDING OF OXYGEN AND TITANIUM (c-3) BINDING OF OXYGEN AND TITANIUM
(ONE TITANIUM ATOM COMBINED TO TWO OXYGEN ATOMS SURROUNDED BY FOUR TITANIUM ATOMS IN 1st LAYER)

[STEP1]

2nd LAYER (c-1) TITANIUM OXIDATION ($Ti^{3+} \rightarrow Ti^{4+}$)

[STEP1]

MICROCHIP AND FILM FORMING METHOD FOR METAL THIN FILM OF MICROCHIP

FIELD OF THE INVENTION

The present invention relates to a microchip and a film forming method for metal thin film of the microchip that is used for a separation, a synthesis, an extraction, and an assay and the like of a slight amount of reagent.

DESCRIPTION OF THE RELATED ART

In recent years, the separation, the synthesis, the extraction, and the assay and the like of a slight amount of the reagent have been performed using a micro reactor consisting of a microchip in which a channel of microscale for the assay is formed on a small substrate such as silicon, silicone, or glass or the like by use of the semiconductor micro fabrication technique.

In the above microchip, a channel (i.e., flow channel), which is referred to as a "micro channel" as well, is provided with a region having various functions such as a reactive region in which a reagent is arranged so that a chip (microchip) feasible for various intended purposes (uses) can be configured. Typical intended purposes (uses) of the microchip include an assays in a field of chemistry, biochemistry, pharmacy, medicine, veterinary such as a gene analysis, a clinical diagnosis, a drug screening or the like, and a synthesis of chemical compound, and environmental measurement and the like.

In the medical field, in a microchip used for a measurement that employs an intermolecular interaction such as an immune reaction or the like in a clinical assay (such as Surface Plasmon Resonance (SPR) measurement technique, a crystal oscillator microbalance (QCM) measurement technique, and a measurement technique using functionalized surface from auric (gold) colloid particles to auric (gold) ultrafine particles, and the like), for example, an antibody (immune body) is fixed (immobilized) in advance inside the channel. As such, the measurement using the microchip is performed that is associated with the antibody antigen reaction which occurs by delivering the reagent including the antigen inside the channel.

Hereinafter, various kinds of Surface Plasmon Resonance sensor (hereinafter also referred to as "SPR sensor") which employs the SPR phenomenon and the microchip that is used therefor will be described.

The SPR phenomenon is the phenomenon that a plasma wave, so called the Surface Plasmon, which exists on a metal thin film, and an evanescent wave, which is generated on the metal surface when the irradiated light emitted from a rear face of the metal thin film is totally reflected, resonate each other so that the reflected light intensity attenuates at a certain angle (i.e., a resonance angle). The resonance angle depends on a refractive index (refractive constant) on the metal surface. The SPR sensor senses, using information of the resonance angle, a status of the metal thin film surface.

FIG. 23 shows a configuration of a certain SPR sensor which has been proposed by Kretschmann.

A main body of the SPR sensor has a structure in which a metal thin film 4 is provided on a prism 8 made of glass that has higher refractive index than in atmospheric air. Monochromatic light such as laser light enters into a boundary face between the prism 8 and the metal thin film 4. The incident angle of the incident light is set to the angle that is equal to or larger than a critical angle at which the total reflection occurs on the boundary face. The monochromatic light is totally reflected at the boundary face and then advances outside the prism 8. At this time, the evanescent wave exudates on the surface of the metal thin film 4. When the wave number of the evanescent wave coincides with the wave number of the Surface Plasmon which is possibly generated on the metal surface, the resonance of the both (hereinafter also referred to as "Surface Plasmon Resonance") occurs, and a portion of an energy of the incident light changes into an energy of the Surface Plasmon wave. As a result, the reflected light from the above mentioned boundary face attenuates.

It should be noted that the Surface Plasmon, on the metal surface, propagates as a compressional wave of electrons in a direction parallel to an advancing direction of the light. For this reason, in order to generate the Surface Plasmon Resonance, the p-polarized light including an oscillating component of an electric field is required to enter in this direction. On the other hand, when the s-polarized light including an oscillation (oscillating component) vertical to the p-polarized light, the Surface Plasmon hardly occurs.

The Surface Plasmon Resonance depends on a wavelength of the incident light, an incident angle, the refractive index distribution of the metal thin film surface and the like. For this reason, in case that the reagent is arranged on the surface of the metal thin film 4, the incident angle of the incident light changes when the Surface Plasmon Resonance occurs, as the refractive index of the metal thin film surface changes.

In other words, the status (condition) of the metal thin film surface can be identified by measuring and analyzing the incident angle when the reflected light intensity attenuates (hereinafter also referred to as "resonance angle").

The SPR sensor has been used for the various kinds of measurements. For example, as disclosed in the Patent Literature 1 (Japanese Patent Application Laid-open Publication No. Hei6-167443A), the SPR sensor can be used for a microscope that measures with high sensitivity information of dielectric substance in the vicinity of the surface and a film thickness distribution of the dielectric thin film.

Also, as disclosed in the Patent Literature 2 (Japanese Patent Application Laid-open Publication No. 2000-55805A), the SPR sensor can be used for detecting the refractive index of solution or the like contacting the metal thin film (for example, a sample such as blood or urine) and a variance thereof, observing a variance in an amount of substance in the solution, and detecting protein, nucleic acid and other bio related substance thereof to which the antibody immobilized on the metal thin film specifically bind (combine) and determining the quantity thereof (i.e., for monitoring the antibody antigen reaction). In other words, the SPR sensor is used as a bio sensor that is used in the fields of biochemistry, molecular biology and medical testing.

FIG. 24 shows an exemplary configuration of the microchip and the SPR sensor using thereof.

Typically, the microchip used as a specimen of the SPR sensor has a structure in which a pair of substrates (i.e., a first microchip substrate 1 and a second microchip substrate 2) are faced each other and are joined together. A minute (microscopic) channel 3 is formed on the surface of at least one of the substrates (i.e., microchannel: for example, approximately, 10 to several hundred μm in width, and 10 to several hundred μm in depth).

The metal thin film 4 is applied to the second microchip substrate 2, and the antibody Ig (i.e., an antigen receptor) is immobilized on the metal thin film 4. The channel 3 is formed in, for example, the first microchip substrate 2. In the microchip configured by joining the first microchip substrate 1 and the second microchip substrate 2 made of glass, the metal thin film 4 and the antibody Ig immobilized on the metal thin film 4 exist within the channel 3.

The specimen including the antigen is introduced from an inflow port (inlet) 3a of the channel 3 and discharged from an outflow port (outlet) 3b.

As described above, in the measurement using the Surface Plasmon Resonance (SPR), the metal thin film 4 is provided on the prism 8 made of the glass with higher refractive index than in the atmospheric air. For this reason, the second microchip substrate 2 in FIG. 24 is required in principle to be the prism 8, as shown in FIG. 23.

In this case, however, the prism 8 is required to be prepared for each of the microchips so that the fabrication cost increases.

Accordingly, it is considered that, with the second microchip substrate 2 being prepared from the glass substrate having the same material as the prism 8, matching oil 7 intervenes that is a medium with substantially the same refractive index as the glass between the second microchip substrate 2 and the prism 8. By doing this, the microchip and the prism 8 optically join each other. According to the above mentioned configuration, the prism 8 is not necessarily required to be prepared for each of the microchips, and when a plurality of measurements are to be performed, it is required only to exchange the microchip.

A light source 6a emitting light onto the metal thin film 4 is, for example, a semiconductor laser equipment, which emits a laser beam with the wavelength of, for example, 670 nm. Light emission from the light source 6a is controlled by a controller, which is not shown in the figures. The laser beam emitted from the light source 6a becomes, after passing through a polarizing element, which is now shown, a laser beam with p-polarization to be irradiated onto the metal thin film 4. The reflected light from the metal thin film 4 is light-received by a CCD 6b (i.e., a solid state image sensing device). Image information from the CCD 6b is transmitted to the controller, which is not shown in figures, and the controller, which has received the image information from the CCD 6b, analyses the received image information and monitors the antibody antigen reaction.

FIG. 25 shows an exemplary configuration of the metal thin film 4, and shows an enlarged sectional view of the portion "A" in FIG. 24.

As the metal thin film 4 that allows the Surface Plasmon Resonance (SPR) to develop, silver, gold, copper, or aluminum or the like is used. In general, the wavelength of the laser beam emitted from an inexpensive semiconductor laser equipment is visible or near infrared. For this reason, gold (Au) is commonly employed that can correspond (be responsive) to such wavelength and also chemically stable. The thickness of the gold film 4a is, for example, 20 to 50 nm.

Furthermore, in order to improve the adhesion (adhesiveness) between the gold film 4a and the second microchip substrate 2 of the glass substrate, a buffer layer 4c is provided between the gold film 4a and the second microchip substrate 2, as disclosed in the Patent Literature 3 (Japanese Patent Application Laid-open Publication No. 2002-257720A). As the buffer layer 4c, for example, a titanium (Ti) film may be provided. The film thickness of the titanium film 4c is, for example, 3 to 5 nm. It should be noted that, in fact, an ultrathin (extremely thin) titanium oxide ($tiO_2$) film 4b exists between the titanium film 4c and the gold film 4a, which is generated with the titanium film surface being oxidized due to oxygen in the atmospheric air.

The metal thin film 4 shown in FIG. 25 is, for example, formed during the processes as described below.

First, a titanium film is provided on the second microchip substrate 2 of the glass substrate by way of the vapor deposition method or the sputtering method or the like. Subsequently, a gold film 4a is formed on the titanium film with the film thickness of 20 to 50 nm by way of the vapor deposition method of the sputtering method.

It should be noted that the second microchip substrate 2 on which the titanium film 4c is formed is likely to be exposed (revealed) in the air during the formatting of the gold film 4a on the titanium film 4c. Thus, titanium oxide film 4b is formed that is a natural oxidization (naturally oxidized) film on the titanium film 4c before the gold film 4a is formed on the titanium film 4c. In other words, titanium oxide film 4b is to be interposed between the titanium film 4c and the gold film 4a. As the titanium oxide film 4b demonstrates the higher hydrophilic property, the metal thin film 4 such as gold is assumed to be capable of densely (firmly) adhering to the surface of the titanium oxide film 4b.

LISTING OF REFERENCES

Patent Literatures

Patent Literature 1: Japanese Patent Application Laid-open Publication No. Hei6-167443A Patent Literature 2: Japanese Patent Application Laid-open Publication No. 2000-55805A Patent Literature 3: Japanese Patent Application Laid-open Publication No. 2002-257720A Patent Literature 4: Japanese Patent Application Laid-open Publication No. 2001-262008A Patent Literature 5: Japanese Patent Application Laid-open Publication No. 2006-187730A Patent Literature 6: Japanese Patent Publication No. 3714338B

SUMMARY OF THE INVENTION

Problems to be Solved by the Invention

The titanium (Ti) film 4c serving as the buffer layer is useful as an adhesive layer that can improve the adhesiveness (adhesion) between the second microchip substrate 2 of the glass substrate and the gold (Au) film. 4a. On the other hand, however, the extinction coefficient of the light is large. For example, the extinction coefficient of the titanium film 4c with respect to the incident light with the wavelength of 670 nm is 3.65, which is sufficiently large.

For this reason, even if the film thickness of the titanium film 4c varies by 1 nm, still the reflected light of the light irradiated onto the rear face of the metal thin film 4 (i.e., the SPR signal) considerably varies.

Accordingly, in order to reduce the individual difference among the microchips, the film thickness of the titanium film 4c is required to be controlled such that the film thicknesses are uniform among individual microchips. However, by employing the vapor deposition method or the sputtering method, it is turned out difficult to control the deviation in the film thickness to be less than 1 nm. In the first place, the film thickness of the titanium film 4c is approximately 3 to 5 nm, as mentioned above. Thus, it is difficult to control the film thickness when forming the film.

Taking the above circumstances into consideration, the buffer layer is required that is capable of improving the adhesiveness between the glass substrate (i.e., the second microchip substrate 2) and the metal thin film for the SPR such as Au film or the like and simultaneously that has the smaller extinction coefficient thereof.

Here, the inventors of the present invention have drawn attention to titanium oxide ($TiO_2$) film that is interposed between the titanium film serving as the buffer layer and the golf (Au) film of the metal thin film in the conventional microchip.

The titanium oxide film has the higher permeability (transmissivity) in a visible range and the smaller extinction coefficient. Also, the titanium oxide film is chemically stable and the surface thereof demonstrates the hydrophilic property. For this reason, the titanium oxide film has the better adhesiveness with the gold film so that the titanium oxide film is useful as the adhesive layer that can improve the adhesiveness between the second microchip substrate of the glass substrate and the gold film. Moreover, as the titanium oxide film has the smaller extinction coefficient in the visible range compared to the titanium film, the deviation in the film thickness of the titanium oxide film less affects the SPR signal. As a result, the film thickness of the titanium oxide film is not required to necessarily achieve higher uniformity of approximately 1 nm in the deviation, as is required in the case of the titanium film.

However, in case that the titanium oxide film serving as the buffer layer for the metal thin film is formed on the glass substrate by use of the conventional film forming method of the titanium oxide film, it is turned out that it entails drawbacks as will be described below.

In general, the titanium oxide film is formed on the surface of the substrate in a way that titanium oxide sol, in which titanium oxide powder or fine titanium oxide particle of approximately 10 nm is dispersed in water or a solvent, or titania sol, in which titanium compound such as titanium alkoxide or the like is dissolved, is applied onto the surface of the substrate, and then sintered at the temperature of, for example, equal to or less than 600 degrees Celsius. The titanium oxide sol or the titania sol is applied by spraying it onto the surface of the substrate with a spray or the like. Similar example is disclosed in the Patent Literature 4 (Japan Patent Application Laid-open Publication No. 2001-26008A).

In this way, in case that the titanium oxide film is immobilized on the surface of the glass substrate, the titanium oxide film is immobilized with physical absorption (adhesion). For this reason, the physical strength of the titanium oxide film on the surface of the glass base material (substrate) differs depending on the film thickness of the titanium oxide film. In other words, as the titanium oxide film is formed relatively thicker on the glass base material, the titanium oxide film is more likely to exfoliate.

Furthermore, the titanium oxide film immobilized on the surface of the glass base material as described above has in general the amorphous structure, which is close to the anatase structure and has the shape (dimension) of particles as shown in FIG. 26. For this reason, even if the gold film 4*a* is formed on the titanium oxide film 4*b* having such structure by way of the vapor deposition method of the sputtering method, the binding state of the titanium oxide film 4*b* and the gold film 4*a* becomes weak.

Furthermore, there is a case that the titanium oxide film 4*b* having a property of the anatase structure is unintentionally exposed partially from the gold film 4*a*. In such a case, even if an organic substance such as protein is immobilized on the gold film 4*a*, still at least a portion of the immobilized protein is decomposed by photocatalytic reaction of the titanium oxide.

The present invention has been made in view of the above mentioned circumstance and its object is to provide a microchip in which the gold thin film such as gold (Au) or the like is applied (formed) on the glass substrate forming the microchip, and that employs the titanium oxide film having a smaller extinction coefficient as a buffer layer provided between the glass substrate and the metal thin film. Another object of the present invention is to provide a method for forming a metal thin film of the glass substrate of the microchip that is capable of forming the titanium oxide film on the surface of the glass substrate in a simplified manner, and that is capable of controlling the film thickness of the titanium oxide film.

Solution to the Problem

FIGS. 1A and 1B show an exemplary configuration of a microchip according to one embodiment of the present invention.

Similarly to the above mentioned exemplary configuration of the microchip used as the specimen of the SPR sensor, the microchip according to the present invention also has a structure in which a pair of substrate (i.e., a first microchip substrate 1 and a second microchip substrate 2) are faced each other and joined together, as shown in FIG. 1A. In the microchip, a fine channel (flow channel) 3 (i.e., a microchannel: for example, approximately 10 to several hundred μm in width and 10 to several hundred μm in depth) is formed on the surface of at least one substrate.

A metal thin film 4 is applied to the second microchip substrate 2, and an antibody (i.e., an antigen receptor) is immobilized on the metal thin film 4. The channel 3 is formed in, for example, the first microchip substrate 1.

The first microchip substrate 1 is made of, for example, silicone resin such as polydimethylsiloxane (PDMS). In the microchip configured by joining the first microchip substrate 1 and the second microchip substrate 2 made of glass, the metal thin film 4 and the antibody immobilized on the metal thin film 4 exist inside the above mentioned channel 3.

The specimen containing the antigen is introduced from an inlet (inflow port) 3*a* of the channel 3, and discharged from an outlet (outflow port) 3*b*.

As shown in FIG. 1B, as the metal thin film 4, for example, gold (Au), which is chemically stable, may be employed, and the thickness of the Au film 4*a* is, for example, 20 to 50 nm.

Also, in order to improve the adhesiveness (adhesion) between the Au film 4*a* and the second microchip substrate 2 of the glass substrate, the titanium oxide ($TiO_2$) film 4*a* is provided as a buffer layer provided between Au and the second microchip substrate 2.

The titanium oxide film is capable of being formed on the substrate (base material) made of glass, by performing the following process 0 to process 3 as shown in FIG. 2 with respect to the substrate that is a molding (compact) made of the glass.

(Process 0)

A surface of a base material W (i.e., the second microchip substrate 2), which is a molding made of the glass for immobilizing titanium oxide, is irradiated with ultraviolet light irradiate from a light source L in an ambient atmosphere containing oxygen and moisture.

Here, as the metal thin film 4 is formed on a portion of the base material W made of glass (i.e., the second microchip substrate 2), in fact, the titanium oxide film is also formed on the portion of the base material W. For this reason, as shown in FIG. 2, a shielding member 5, which has an aperture (opening) 5a corresponding to a region in which the titanium oxide film is formed, is provided on the surface of the base material W.

With the base material W made of glass being irradiated with the ultraviolet light through the aperture 5a, as described above, a siloxane bond (binding) portion on the glass surface is cleaved, and oxygen (O) bound to silicon (Si) is exposed on the glass surface, as shown in the process 0 in FIG. 2. The exposed oxygen binds to hydrogen (H) of the moisture contained in the ambient atmosphere to form hydroxyl group. In other words, it is assumed that a terminal of the glass surface ultimately becomes the hydroxyl group (hydroxyl group terminated).

It should be noted that, in fact, the glass has an amorphous structure, as shown in FIG. 2, and silicon and oxygen are irregularly arranged. However, here, for the purpose of facilitating the understanding, the structure of the glass surface is shown as the siloxane structure in which silicon and oxygen are aligned in a straight chain. It should be also noted that, although silicate glass, which has a skeleton of silicon dioxide, is described as an example of the glass, the present embodiment is not limited to this particular example. For example, oxide glass such as borate glass may be employed. In such another glass, it is also considered that the terminal of the glass surface becomes the hydroxyl group.

As the light used for irradiating in the above process 0, vacuum ultraviolet light, which is absorbed in the glass and also contains light with the wavelength equal to or less than 200 nm that is light having the wavelength exceeding an activation energy of the glass, irradiates the above mentioned surface. More particularly, as will be described below in the embodiments according to the present invention, for example, monochromatic light having a central wavelength at the wavelength of 172 nm, which is emitted from a vacuum ultraviolet excimer lamp, may irradiate the above mentioned surface.

(Process 1)

The above mentioned base material is immersed in mixed solution of titanium chloride aqueous solution and nitrite ion contained aqueous solution (for example, sodium nitrite aqueous solution) (Process 1(a) in FIG. 2).

As a result of being immersed, as shown in the Process 1(b) in FIG. 2, hydrogen disengages from the hydroxyl group terminal (terminal of hydroxyl group) of the base material made of the glass, and the oxygen and titanium ions in the mixed solution bind each other.

Subsequently, at the terminal of cyclic olefin based base material, of which olefin ring is cleaved, oxidation of the titanium ions with nitrite ions, binding of the oxidized titanium ions and oxygen, and binding of the bound oxygen and the titanium ion are repeatedly performed. Thus, the titanium oxide film is grown on the ultraviolet light irradiated surface of the base material made of the glass (Process 1(c) in FIG. 2).

(Process 2)

After the prescribed time elapses, as shown in the Process 2 in FIG. 2, the base material is pulled (lifted) out from the above mentioned mixed solution and washed (cleaned). In other words, the reaction is stopped with pure water washing (cleaning).

As the immersion time elapses, the film thickness of the titanium oxide becomes thicker on the base material. Nevertheless, the film forming reaction of the titanium oxide film is stopped by pulling out the base material from the mixed solution and washing it. It is therefore considered that the film thickness of the titanium oxide can be controlled by controlling the immersion time.

(Process 3)

The base material after washing is dried (air dried) at an ambient temperature.

(Process 4)

After the above mentioned Process 1 to Process 3, the titanium oxide film 4b is formed on a portion (i.e., a portion of the aperture 5a of the shielding member 5) of the base material W (i.e., the second microchip substrate 2 of the glass substrate).

Subsequently, the base material W after the Process 3 is disposed in a film forming equipment that implements the film forming by way of the vapor deposition method or the sputtering method or the like. Then, as shown in FIG. 3, a gold (Au) film 4a is formed on the base material W at the side of the shielding member.

(Process 5)

After the gold (Au) film is formed in the Process 4, as shown in FIG. 3, the shielding member 5 is exfoliated from the second microchip substrate 2 (i.e., base member W). As a result of being exfoliated, the Au film 4a is, except for those formed on the titanium oxide film 4b, removed from the second microchip substrate 2 along with the shielding member 5.

(Process 6)

A first microchip substrate 1 is laminated on the second microchip substrate 2 to be joined together, as shown in FIG. 3.

By performing the above mentioned processes, the microchip is formed in which the metal thin film 4 is applied inside the channel 3.

As such, according to one embodiment of the present invention, the above mentioned problem to be solved is able to be solved as described below.

(1) In the microchip that includes a substrate made of glass, on which a metal thin film is formed, and a channel, which is formed in a space containing the metal thin film, a titanium oxide film is provided between the substrate and the metal thin film, the titanium oxide film contacts the substrate with one face and contacts the metal thin film with the other face.

(2) Also, according to another embodiment of the present invention, a metal thin film having a titanium oxide film provided between the substrate and the metal thin film is formed as follows:

(a) Providing a shielding member having an aperture of which dimension corresponds to a size of the metal thin film to be deposited on a surface of the substrate made of glass, irradiating vacuum ultraviolet light having a wavelength of equal to or less than 200 nm onto a surface of the substrate at the shielding member side in an ambient atmosphere containing oxygen and moisture, immersing the substrate in mixed solution of titanium chlorite aqueous solution and nitrite ion contained aqueous solution, pulling out the substrate from the mixed solution after a prescribed time elapses since the substrate is immersed in the mixed solution and washing the substrate with water to stop a film forming process, and drying a base member (the substrate) after water washing at an ambient temperature.

(b) Depositing a metal thin film on a surface of the substrate at the shielding member side.

(c) Removing the shielding member from the substrate.

(3) According to another embodiment of the present invention, the metal thin film may be composed from any of gold (Au), platinum (Pt), rhodium (Rh), palladium (Pd), and palladium-platinum alloy (Pd—Pt alloy).

Advantageous Effect of the Invention

According to the above mentioned embodiments of the present invention, an advantageous effect can be achieved as follows.

(1) The microchip according to the present invention employs a titanium oxide film having a smaller extinction coefficient as a buffer layer for the metal thin film to be applied onto the substrate made of glass. Thus, the deviation in the film thickness of the buffer layer less affects the SPR signals. As a result, the film thickness of the titanium oxide film is not necessarily required to accomplish the higher uniformity of approximately 1 nm, as in the case of the titanium film.

(2) The titanium oxide film has a surface with hydrophilic property, and also has a better adhesiveness with the metal thin film such as gold. As a result, the titanium oxide film is useful (effective) as an adhesive layer for improving the adhesiveness between the glass substrate and the metal thin film.

(3) According to the present invention, the light containing the ultraviolet light with the wavelength equal to or less than 200 nm is irradiated onto the substrate surface made of glass through the shielding member having an aperture. Subsequently, the base material is immersed into the mixed solution of the titanium chloride aqueous solution and the aqueous solution containing nitrite ions so that the titanium oxide film is formed on the substrate surface made of the glass. Thus, a burning process, which heats the titanium oxide on the base material up to several hundred degrees Celsius for crystallization, is not necessarily required so that particles (granulae) of the titanium oxide due to the heating process is not likely to be generated. As a result, it can accomplish the better binding state between the titanium oxide film and the gold film, and the titanium oxide film is not likely to be exposed from a portion of the gold film.

(4) The film thickness of the titanium oxide film becomes thicker on the base material, as the immersion time elapses. Thus, the film thickness of the titanium oxide film can be easily controlled by controlling the immersion (immersing) time.

(5) Also, according to the present invention, the titanium oxide film is formed on the glass substrate by chemical binding. Thus, the physical strength of the titanium oxide film on the glass base material surface does not depend on the film thickness of the titanium oxide film. In other words, it makes it possible to form the titanium oxide that firmly binds to the glass base material.

(6) Furthermore, because the titanium oxide is not formed by use of the hydrolysis reaction, the solution temperature is not necessarily required to be set to a higher temperature than an ambient temperature.

(7) The titanium oxide film formed according to the present invention has the photocatalytic function of the anatase type titanium oxide film, as well as the higher transparency characteristic of the rutile type titanium oxide film. Thus, the titanium oxide film that is formed on the glass substrate according to the present invention has the smaller extinction coefficient. As a result, the deviation in the film thickness of the titanium oxide film is not likely to affect the above mentioned SPR signals.

(8) As the titanium oxide film formed according to the present invention has the hydrophilic surface, when the gold film is formed on this type of titanium oxide film by use of the vapor deposition method or the sputtering method, the binding state between the titanium oxide film and the gold film becomes stronger.

The above mentioned purpose, embodiments and the advantageous effects of the present invention, and also the other purpose, embodiments and the advantageous effects, which has not mentioned above, will be apparent from the following embodiments for embodying the present invention (the detailed description of the present invention), by referring to the accompanying drawings and the attached claims for those skilled in the art.

DETAILED DESCRIPTION OF THE INVENTION

1. Processes 1 to 3 and Actions Thereof

Hereinafter, first, each of treatments in processes according to one embodiment of the present invention will be in turn described in detail.

In the present embodiment, as mentioned above, the following processes 0 to 3 are in turn performed with respect to a second microchip substrate 2 made of glass so as to form a titanium oxide film on a portion of the second microchip substrate 2 made of the glass.

(Process 0)

Figure 2:
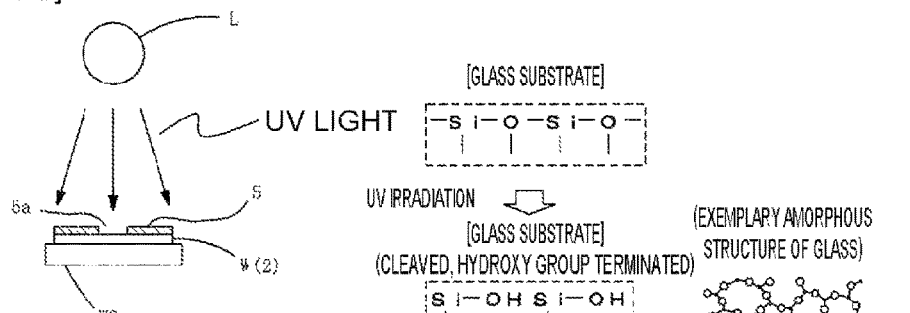
FIG. 2 is a schematic diagram showing an outline of processes for forming a titanium oxide film on a base material made of, for example, glass according to one embodiment of the present invention.
Figure 2:
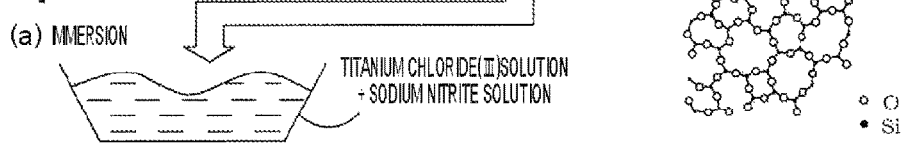
Figure 2:
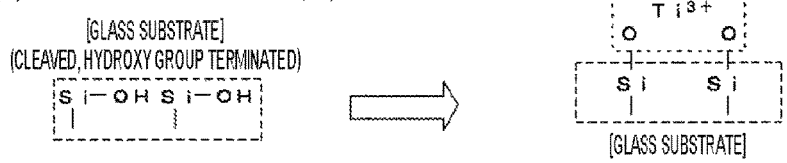
Figure 2:

A shielding member 5 is provided on one face of the second microchip substrate 2, the shielding member 5 has an aperture 5a of which dimension corresponds to a region on which a titanium oxide film is to be formed, as shown in FIG. 2. Then, a surface of the second microchip substrate 2 made of the glass to immobilize titanium oxide is irradiated with ultraviolet light in an ambient atmosphere containing oxygen and moisture.

(Process 1)

The second microchip substrate 2 is immersed in mixed solution of titanium chloride aqueous solution and nitrite ion contained aqueous solution (for example, sodium nitrite aqueous solution).

(Process 2)

After the prescribed time elapses, the second microchip substrate is pull out from the above mentioned mixed solution and washed (cleaned) with purified water. (By doing this, the reaction is stopped).

(Process 3)

The substrate after washing is air dried (dried) at an ambient temperature.

As mentioned above, in the Process 1, the second microchip substrate 2 is irradiated with the ultraviolet light under an air atmosphere containing oxygen through the shielding member having the aperture of which dimension corresponds to the region on which the titanium oxide film is to be formed.

The above mentioned shielding member may be a stencil having the aperture which is made of, for example, silicone or stainless. The shielding member is arranged and immobilized on one face of the second microchip substrate 2 with a holder or the like, which is not shown.

It has been confirmed that the Process 0 employed in the present embodiment performs a following action with respect to the second microchip substrate 2 made of glass (hereinafter also referred to as "glass molding" or "glass compact").

(i) A surface of the molding is activated with the surface of the second microchip substrate 2 made of the glass (the glass molding) being irradiated with the ultraviolet light. More particularly, the cleavage of the binding portion between the metallic atom or the like and oxygen occurs on the surface of the molding. For example, in the case of common silicate glass, the cleavage occurs in a portion of a siloxane bond (linkage).

In order to allow the cleavage in the portion of the siloxane bond to be generated, certain light is required to irradiate that is absorbed in the glass and that has the wavelength exceeding the activation energy of the glass. More particularly, when the surface of the molding made of the glass (silicate glass) is irradiated with the vacuum ultraviolet light having the wavelength equal to or less than 200 nm, the cleavage of the portion of the siloxane bond occurs on the surface of the molding.

More particularly, according to the experiment conducted by the inventors of the present invention, it is turned out that the surface of the molding is preferably irradiated with the light having the wavelength equal to or less than 180 nm in order to assure the cleavage in the portion of the siloxane bond.

(ii) Subsequently, the above mentioned activated molding surface and hydrogen in the air bind, and the glass surface becomes the hydroxyl group terminated (the terminal of the hydroxyl group). In other words, oxygen (O) is exposed on the glass surface by the above mentioned cleavage.

The exposed oxygen binds to hydrogen (H) in moisture contained in the atmosphere to form the hydroxyl group. Thus, it is assumed that the terminal of the glass substrate ultimately becomes the hydroxyl group.

Subsequently, by applying the following Processes 1, 2 and 3, it has been confirmed that the titanium oxide film having a uniform film thickness is formed on the above mentioned molding surface. It should be noted that the Process 1, in which the base material is immersed in the mixed solution of the titanium chloride aqueous solution and nitride ion contained aqueous solution, can be performed at an ambient temperature without requiring a heating process.

It should be also noted that, when irradiating the vacuum ultraviolet light having the wavelength equal to or less than 180 nm, an incidental effect can also be significantly achieved that a contamination of an organic substance or the like adhered to the glass surface can be decomposed. The contamination of the organic substance or the like may constitute a reaction inhibition (inhibiting) substance against the reaction for forming the titanium oxide film in the Process 1, which will be described below. Thus, in the Process 0, it is particularly preferable to irradiate the vacuum ultraviolet light having the wavelength equal to or less than 180 nm.

It is assumed that a mechanism is approximately as the followings in which the titanium oxide is immobilized on the second microchip substrate 2 made of the glass (the glass molding) according to the method of the present embodiment for forming the titanium oxide film on the base material.

Figure 4A:
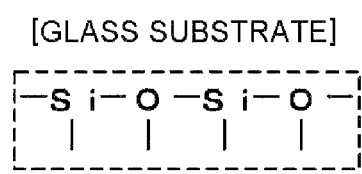
FIG. 4A is a view showing an initial state of the glass substrate in the process 0 of FIG. 2.
Figure 4B:
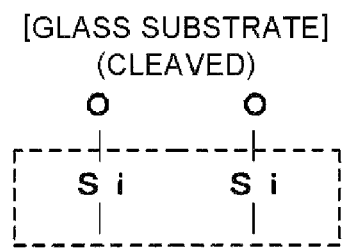
FIG. 4B is a view showing the cleavage of an olefin ring of the glass substrate in the process 0 of FIG. 2.
Figure 4C:
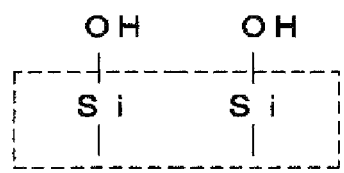
FIG. 4C is a view showing oxygen being introduced into an olefin ring of the glass substrate in the process 0 of FIG. 2.

Referring now to FIGS. 4A, 4B and 4C, the cleavage of the binding portion between the metallic atoms or the like and oxygen and the formation of the hydroxyl group terminal in the Process 0 will be explained. Although an example of the silicate glass, which has a skeleton of silicon dioxide, will be explained below, the glass in the present embodiment is not limited to those explained below.

In the Process 0, the glass molding is irradiated with the light including the ultraviolet light having the wavelength equal to or less than 200 nm (in particular, the vacuum ultraviolet light (hereinafter referred to as "VUV") having the wavelength equal to or less than 180 nm) (FIG. 4A to FIG. 4B). Thus, as shown in FIG. 4B, the cleavage in the binding portion of the metallic atoms or the like (silicon (Si) in the example of FIGS. 4A, 4B and 4C) and oxygen (O) occurs. Subsequently, as shown in FIG. 4C, hydrogen is introduced into the cleavage (cleaved) portion from moisture in the atmospheric air, and it is assumed that the terminal of the glass surface ultimately becomes hydroxyl group (hydroxyl group terminated).

Next, referring now to FIG. 5 to FIG. 12, forming the titanium oxide film in the Process 1 will be explained.

Figure 5:
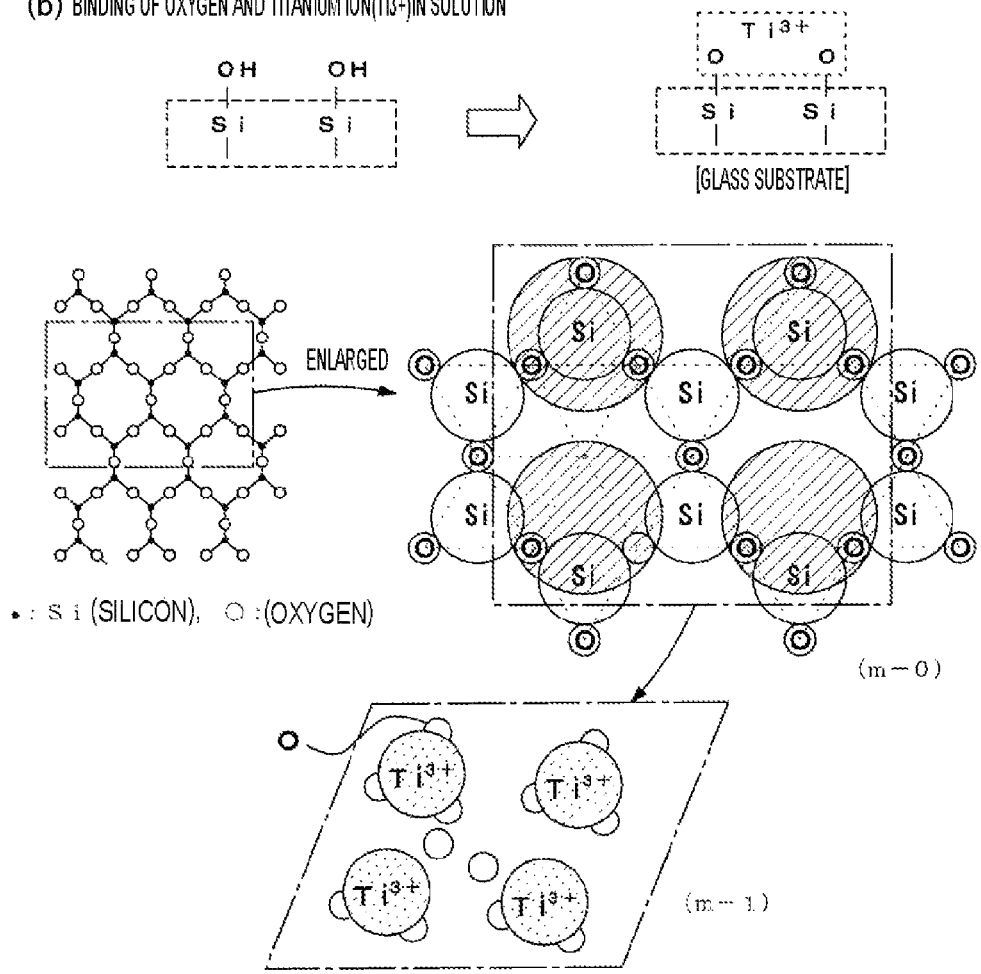
FIG. 5 is a view (1) showing the titanium oxide film being formed in the process 1 of FIG. 2.

In the Process 1 in FIG. 2, as shown in the Process (a) in FIG. 5, the glass molding irradiated with the VUV is immersed in the mixed solution of the titanium chloride (III) aqueous solution ($TiCl_3$ aqueous solution) and sodium nitrite aqueous solution ($NaNO_2$ aqueous solution). The above mentioned mixed solution contains titanium ions ($Ti^{3+}$) and nitrite ions ($NO^{2-}$).

As a result of the immersion, as shown in the Process (b) in FIG. 5, hydrogen is disengaged from the hydroxyl group terminal of the glass molding, and oxygen binds to a titanium ion in the mixed solution.

Here, for facilitating understanding, it is assumed that silicon dioxide forming the glass (silicate glass) has a crystal structure such as a quartz crystal.

The schematic diagram is shown in (m-0) and (m-1) in FIG. 5 that oxygen and titanium ion bind together in the crystal structure. A circle with hatched lines in FIG. 5 denotes titanium atom (ion).

According to the experimental result, which will be described below, a transparent (i.e., a rutile type) titanium oxide film has been formed by applying the Processes 0 to 3. From the experimental result, as shown in the schematic diagram in (m-1) in FIG. 5, it is assumed that the titanium molecules bound (combined) to oxygen distribute such that four titanium molecules are arranged in a square shape.

In other words, the VUV irradiation allows the binding portion of silicon (Si) and oxygen (O) to be cleaved. The distribution of the hydroxyl group terminal exposed on the glass surface corresponds to the distribution of oxygen atoms in the mixed solution to be exposed on the glass surface. As the titanium ion binds to the exposed oxygen atom, the arrangement of the titanium ions depends on the above mentioned distribution of the oxygen atoms.

Furthermore, the distribution of the titanium ions bound (combined) to oxygen is the distribution that corresponds to the bond (binding) distance of the titanium oxide. As such, the arrangement of titanium has the distribution demonstrating the rutile type tetragonal system.

In other words, the rutile type becomes dominant in the molecule structure of the titanium oxide film which is formed according to the method of the present embodiment for forming the titanium oxide film.

As apparent from the schematic diagram in (m-1) in FIG. 5, a first tier of the cubical crystal is formed with four titanium atoms on the surface of the glass (silicate glass) molding in a state that the binding portion of silicon (Si) and oxygen (O) is cleaved by being irradiated with the vacuum ultraviolet light in the atmospheric air containing oxygen and moisture. It should be noted that two oxygen atoms are distributed in the square composed of four titanium atoms.

By the above mentioned immersion, as the time elapses, the titanium oxide film are grown, as shown in FIGS. 6 to 12. In other words, as shown the Process (c) in FIG. 6, [(titanium oxidation)->(binding of titanium and oxygen)] is repeatedly performed.

Figure 6:
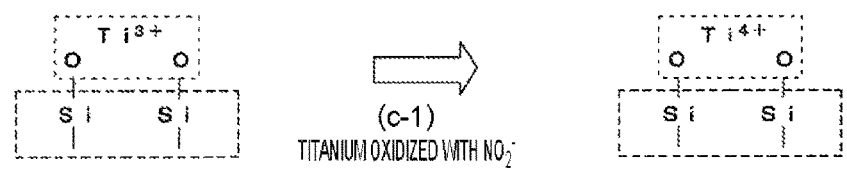
FIG. 6 is a view (2) showing the titanium oxide film being formed in the process 1 of FIG. 2.
Figure 6:
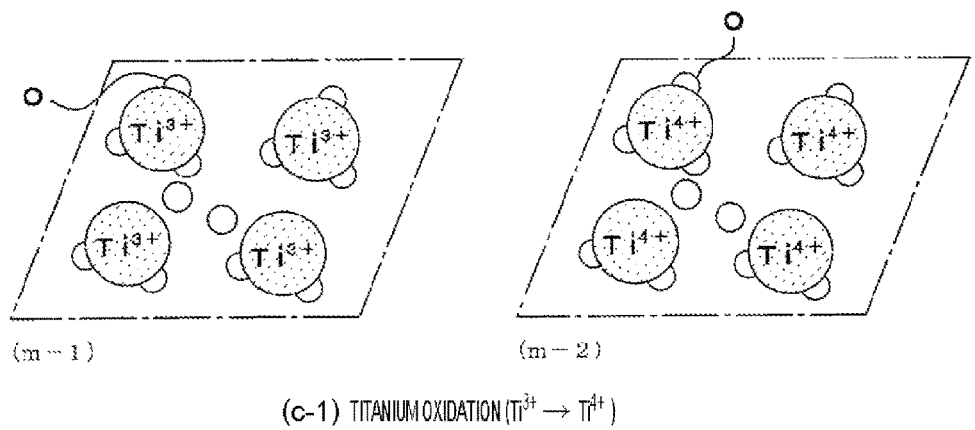

First, as shown in the Process (c-1) in FIG. 6, titanium ion, which binds to oxygen in the glass molding is oxidized with nitrite ions, which is coexistent with the titanium ions in the mixed solution, and $Ti^{3+}$ is transformed to $Ti^{4+}$ (as shown in the schematic diagram in (m-2) in FIG. 6.)

Figure 7:
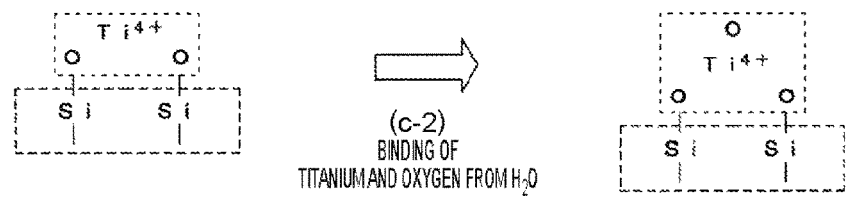
FIG. 7 is a view (3) showing the titanium oxide film being formed in the process 1 of FIG. 2.
Figure 7:
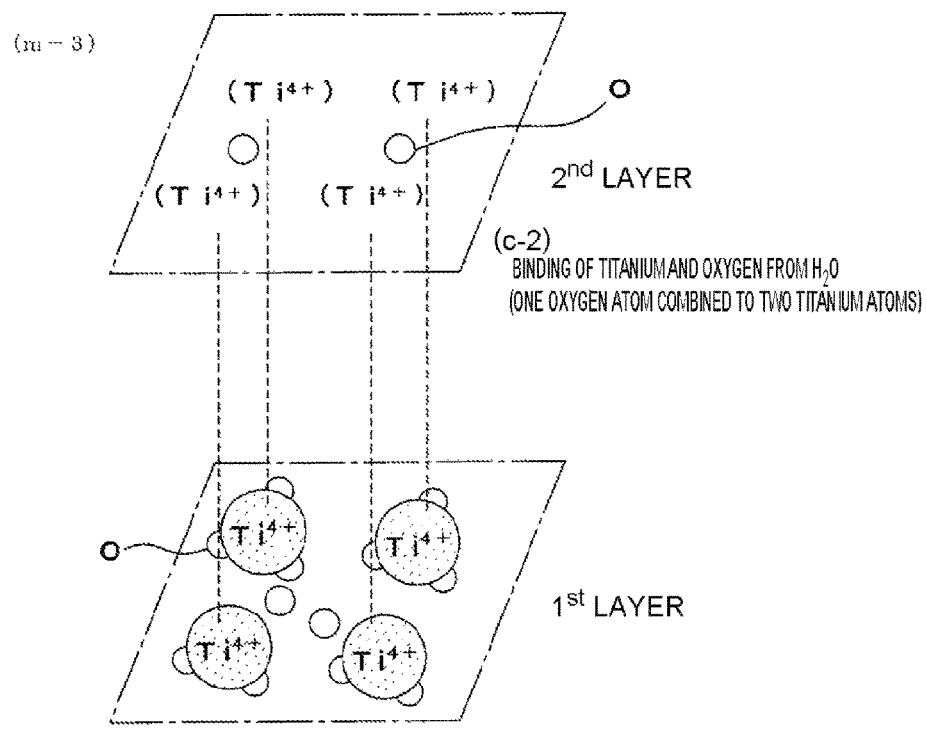

The above oxidized titanium ion binds, as shown in the Process (c-2) in FIG. 7, oxygen supplied from the moisture in the mixed solution. For the sake of simplicity, the first tier of the cubical crystal, which is composed of the square constituted with four titanium atoms (titanium ions) and two oxygen atoms distributed in the square, as shown in the schematic diagram in (m-3) in FIG. 7, is referred to as a "first layer".

The binding of the titanium ion and the oxygen atom in the Process (c-2) in FIG. 7 is performed by binding one oxygen atom to two titanium ions in the first layer. As the first layer contains four titanium ions, the number of oxygen atoms to be bound (combined) is (counts) two. For the sake of simplicity, a region in which two oxygen atoms are located is, as shown in (m-3) in FIG. 7, referred to as a "second layer".

Figure 8:
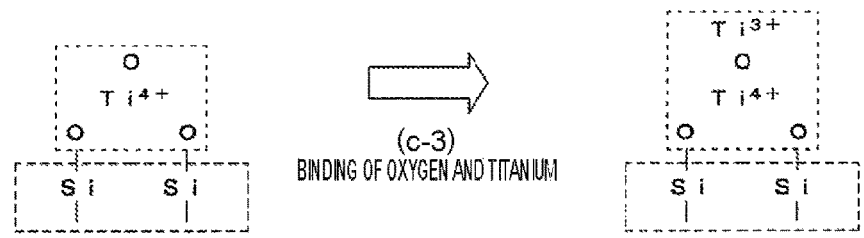
FIG. 8 is a view (4) showing the titanium oxide film being formed in the process 1 of FIG. 2.
Figure 8:
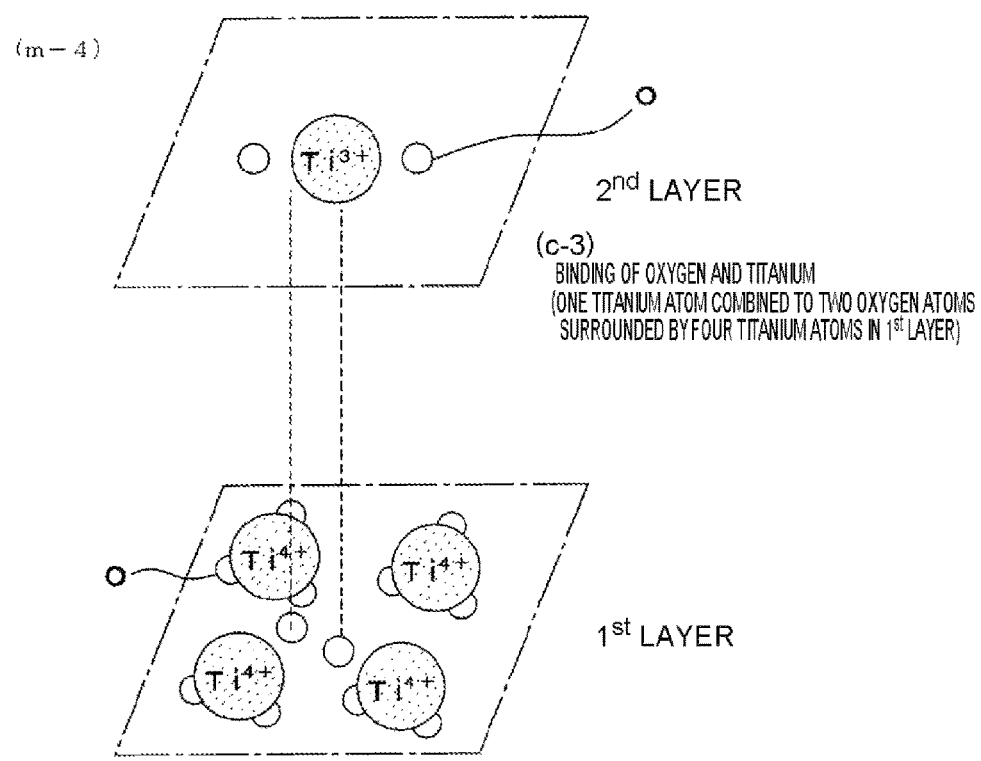

Subsequently, as shown in the Process (c-3) in FIG. 8, the oxygen atom binds to the titanium ion in the mixed solution. As shown in the schematic diagram in (m-4) FIG. 8, two oxygen atoms located in the first layer bind to one titanium ion.

Figure 9:
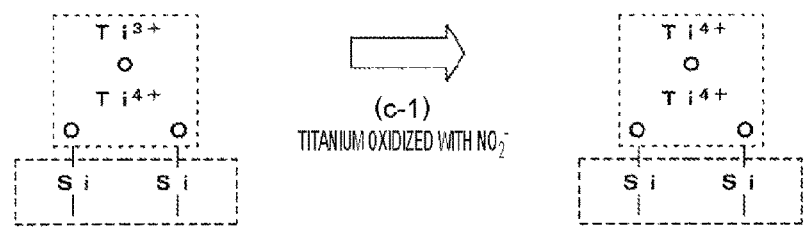
FIG. 9 is a view (5) showing the titanium oxide film being formed in the process 1 of FIG. 2.
Figure 9:
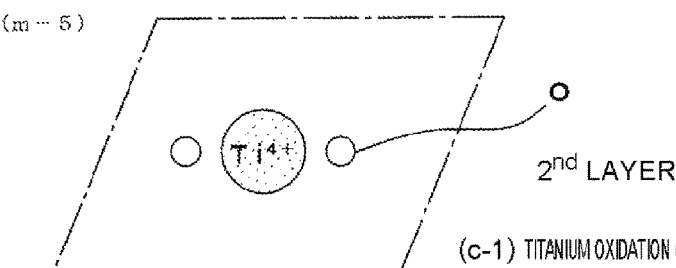

Then, as shown in the Process (c-1) in FIG. 9 and the schematic diagram in (m-5) in FIG. 9, one titanium ion, which is introduced as above described, is oxidized with the nitrite ions, and $Ti^{3+}$ is transformed to $Ti^{4+}$.

Figure 10:
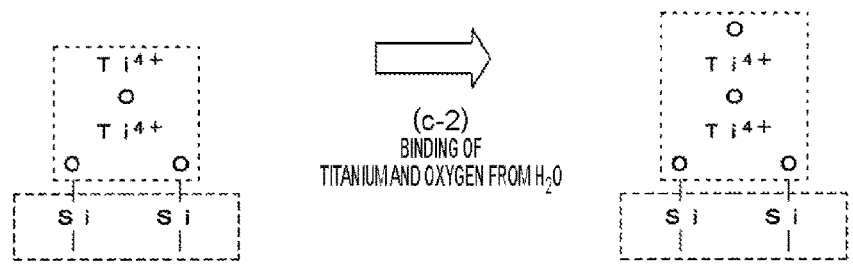
FIG. 10 is a view (6) showing the titanium oxide film being formed in the process 1 of FIG. 2.
Figure 10:
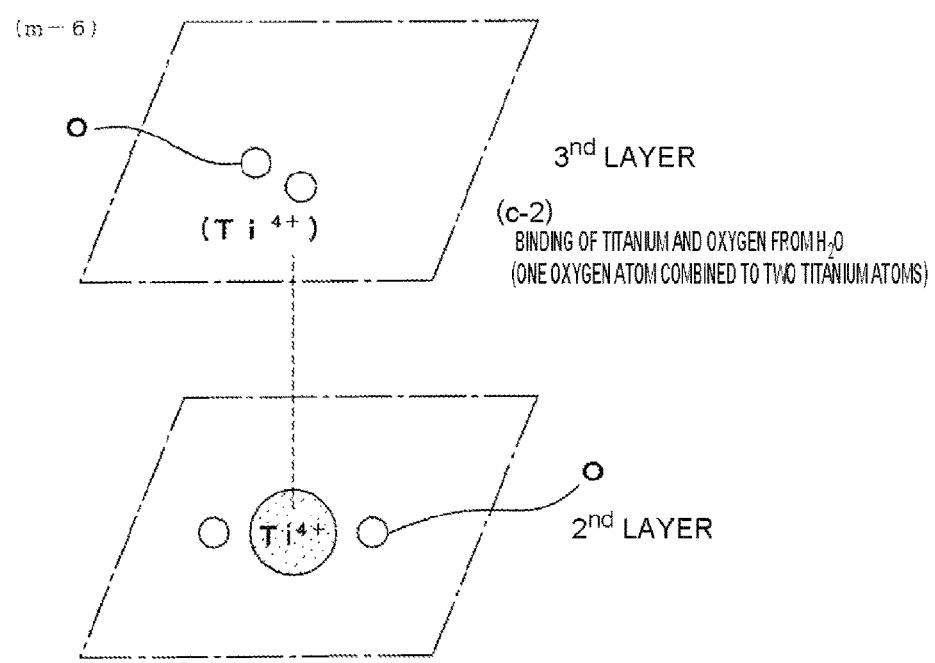

The oxidized titanium ion binds, as shown in the Process (c-2) in FIG. 10, to oxygen supplied from the moisture in the mixed solution.

More particularly, as shown in the schematic diagram (m-6) in FIG. 10, two oxygen atoms bind to one titanium ion in the second layer. For the sake of simplicity, a region in which two oxygen atoms are located is referred to as a "third layer".

Figure 11:
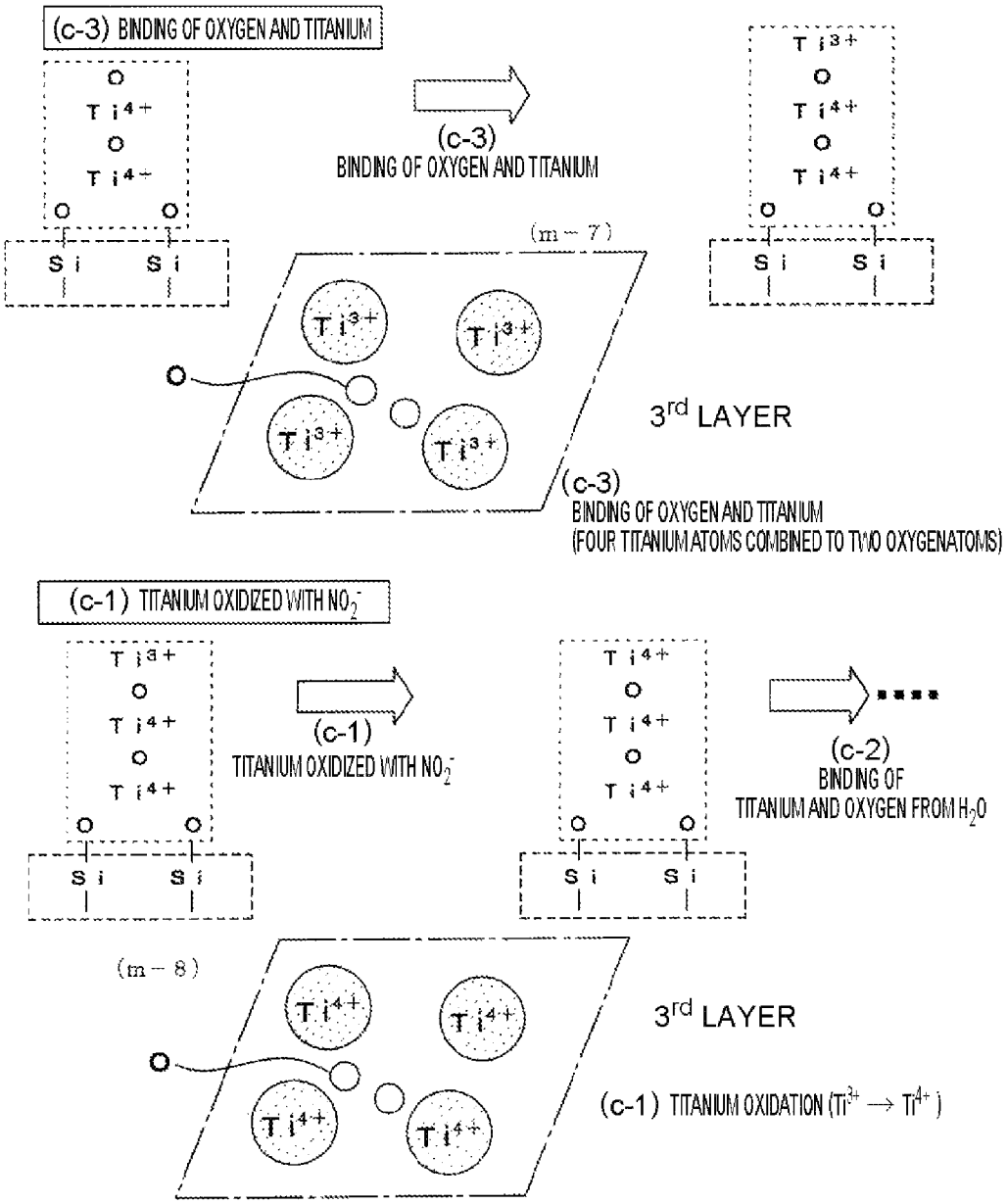
FIG. 11 is a view (7) showing the titanium oxide film being formed in the process 1 of FIG. 2.

Yet subsequently, as shown in the Process (c-3) in FIG. 11, the oxygen atom binds to the titanium ion in the mixed solution. More particularly, as shown in the schematic diagram (m-7) in FIG. 11, two oxygen atoms in the third layer bind to four titanium ions.

Yet subsequently, as shown in the Process (c-1) in FIG. 11 and the schematic diagram (m-8) in FIG. 11, four titanium ions are oxidized with the nitrite ions.

After then, the above mentioned processes, i.e., [(c-2): the binding of the oxidized titanium ion to oxygen], [(c-3): the binding of the bound (combined) oxygen to the titanium ion], and then [(c-1): the oxidization of the titanium ion with the nitrite ion], are repeatedly performed.

Figure 12:
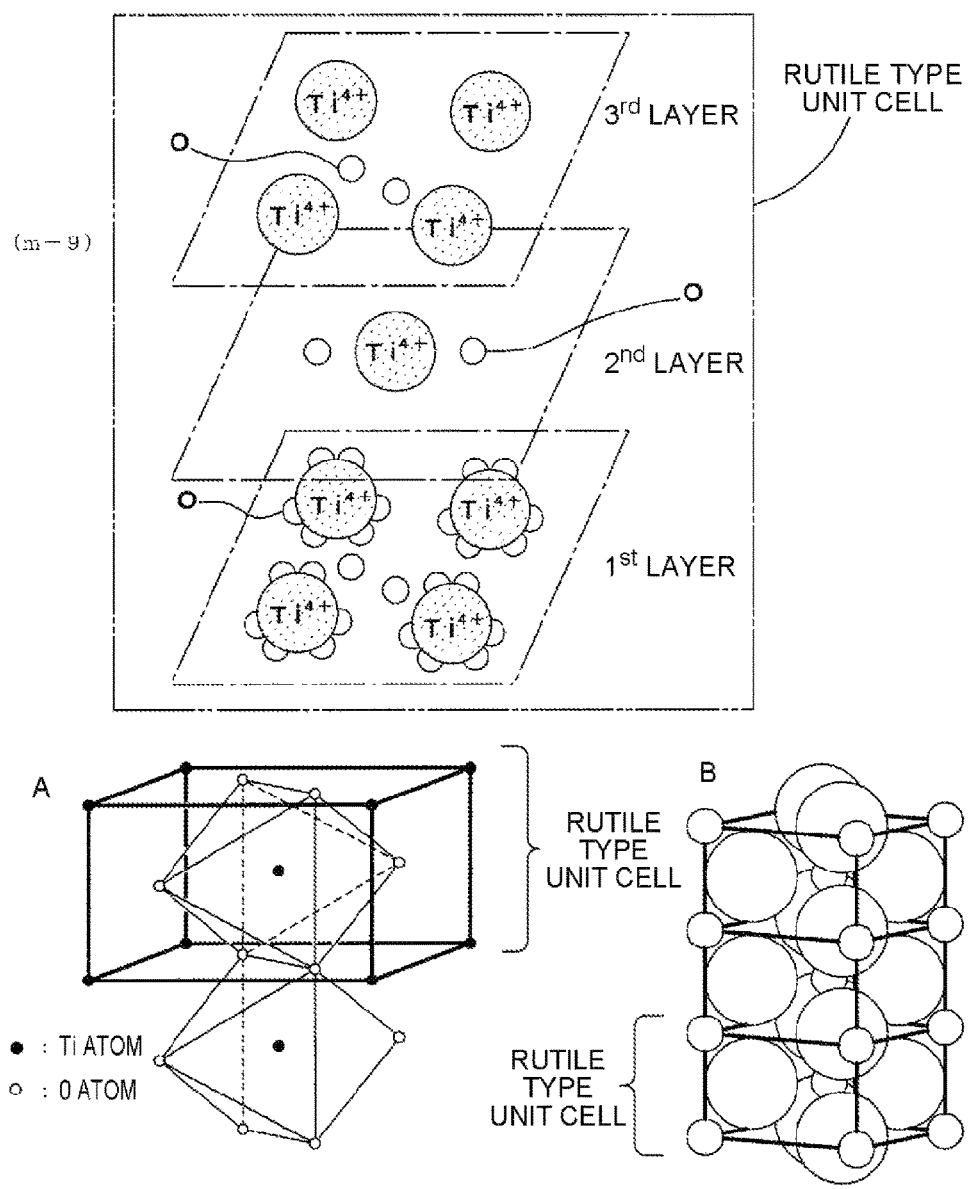
FIG. 12 is a view (8) showing the titanium oxide film being formed in the process 1 of FIG. 2.

In the titanium oxide film, which has grown by laminating (accumulating) in the order of the first layer, the second layer, and the third layer, as shown in the schematic diagram (m-9) in FIG. 12, the rutile type (structure) becomes dominant as shown in FIGS. 12A and 12B.

For this reason, the titanium oxide film formed according to the present invention demonstrates a higher transparency. In other words, as the light is hardly absorbed at the wavelength region 300 to 700 nm, the titanium oxide film can demonstrate an extremely higher transparency.

As described above, in the process 1, at the terminal of a glass molding at which the siloxane binding is cleaved, (c-1) the oxidization of the titanium ions with the nitrite ions; (c-2) the binding of the oxidized titanium ion to oxygen; and (c-3) the binding of the bound (combined) oxygen to the titanium ions, are repeatedly performed. As a result, it is assumed that the titanium oxide film is grown on the VUV irradiated surface of the glass molding.

In other words, in the VUV irradiated region on the glass molding surface, which is immersed in the mixed solution of titanium chloride (III) aqueous solution ($TiCl_3$ aqueous solution) and sodium nitrite aqueous solution ($NaNO_2$ aqueous solution), the titanium oxide is formed according to the following reaction formula:

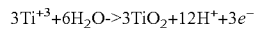

$$3Ti^{+3}+6H_2O \rightarrow 3TiO_2+12H^{+}+3e^{-}$$

Figure 1A:
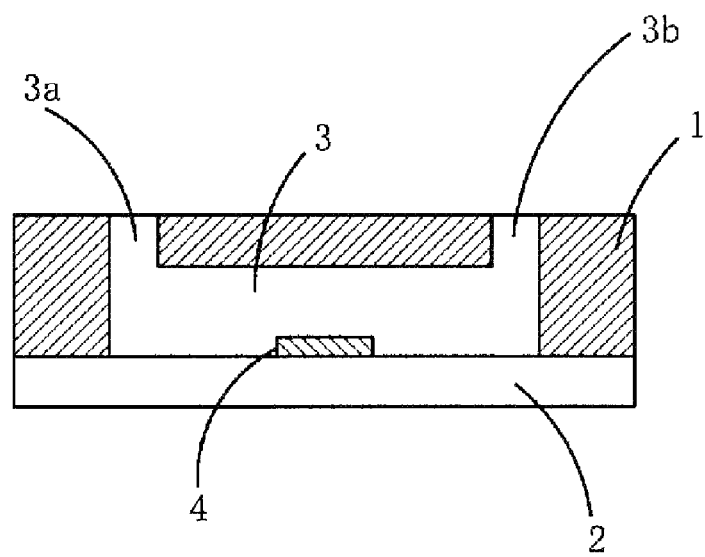
FIG. 1A shows an exemplary configuration of a microchip according to one embodiment of the present invention.
Figure 1B:
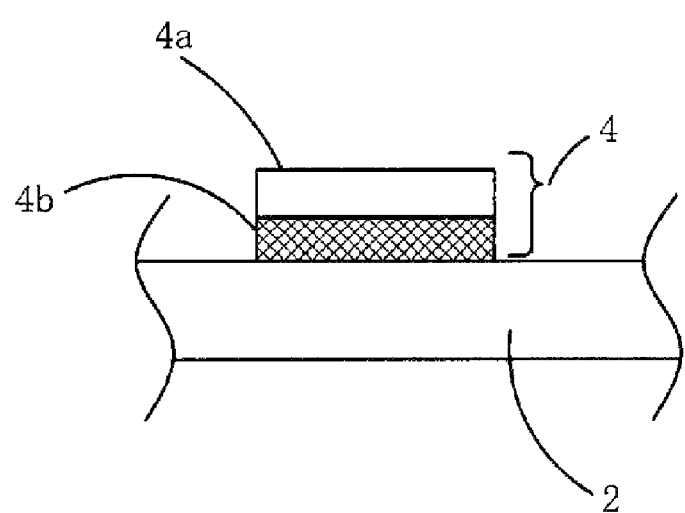
FIG. 1B shows an exemplary configuration of a metal thin film 4 of FIG. 1A.

It should be noted that in forming the titanium oxide film in the Process 1, which has been explained referring to FIGS. 5 to 12, it is presumed that, as mentioned above, silicon dioxide, which forms the glass (silicate glass), has a crystal structure such as a quartz crystal. In fact, as shown in FIGS. 1A and 1B, the glass may have an amorphous structure, and silicon and oxygen may be irregularly arranged.

As mentioned above, it is assumed that the crystal structure of the titanium oxide, which is formed on the glass molding, is defined by the location of oxygen existing on the surface of the glass molding. For this reason, when silicon dioxide forming the glass (silicate glass) has the crystal structure such as the quartz crystal, the distribution of the titanium ions to be bound (combined) to the oxygen atom exposed on the surface demonstrates the distribution that the crystal structure of the growing titanium oxide film is such that it becomes the rutile type tetragonal system. On the other hand, in the glass with the amorphous structure, the arrangement of the oxygen atoms exposed on the glass surface in the Process 0 (that is, the distribution of the titanium ions to be bound to oxygen) does not necessarily become the distribution that the crystal structure of the glowing titanium oxide film is such that it becomes the rutile type tetragonal system.

With respect to the arrangement of the oxygen atoms exposed on the surface, in a region in which the arrangement (distance) of the titanium ions to be bound to the oxygen atoms substantially corresponds to the lattice constant of the anatase type titanium oxide, it is assumed that the anatase type titanium oxide is formed.

In other words, in the titanium oxide film formed on the surface of the glass molding with the amorphous structure, the rutile type titanium oxide and the anatase type titanium oxide are intermingled (are mixed).

As mentioned above, after the glass molding is immersed in the above mentioned mixed solution for a prescribed time, in the Process 2, the class compact is pulled out from the mixed solution and washed (cleaned) with the purified water or the like to stop the above mentioned reaction.

As the immersion (immersing) time into the above mentioned mixed solution elapses, the film thickness of the titanium oxide on the base material becomes thicker. However, by pulling out the base material from the mixed solution and washing the base material, the reaction for forming the titanium oxide film can be stopped. As such, it is assumed that the film thickness of the titanium oxide film can be controlled by controlling the immersion time.

In the Process 3, the above mentioned base material after washing is dried (air dried) at an ambient temperature.

2. Process 4 to Process 5

Figure 3:
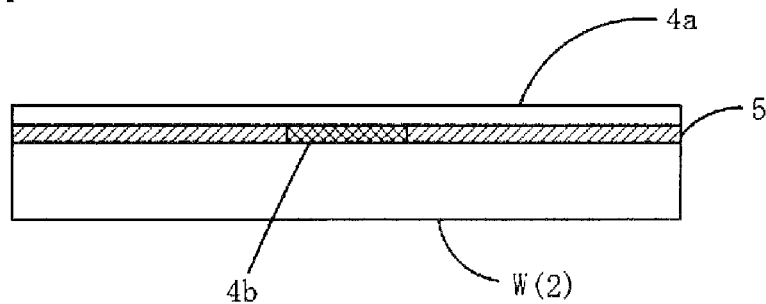
FIG. 3 is a schematic diagram showing processes in which the metal thin film having the titanium oxide film is formed as shown in FIG. 2, a first and second microchip substrates are joined together to constitute the microchip according to one embodiment of the present invention.
Figure 3:
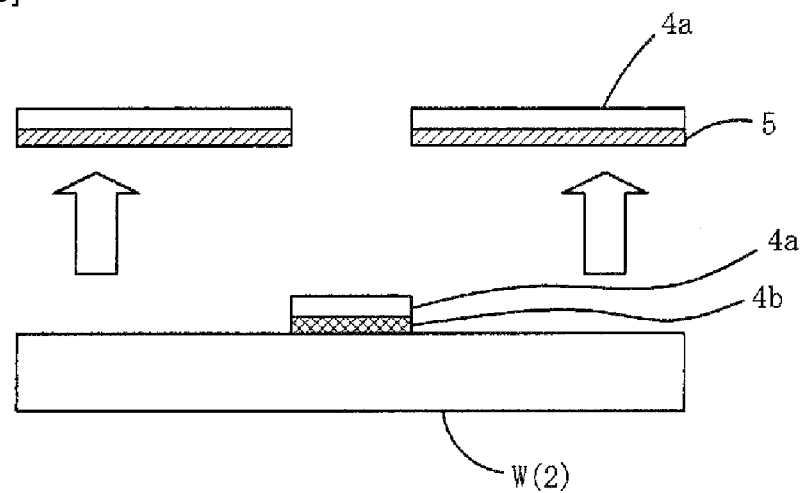
Figure 3:
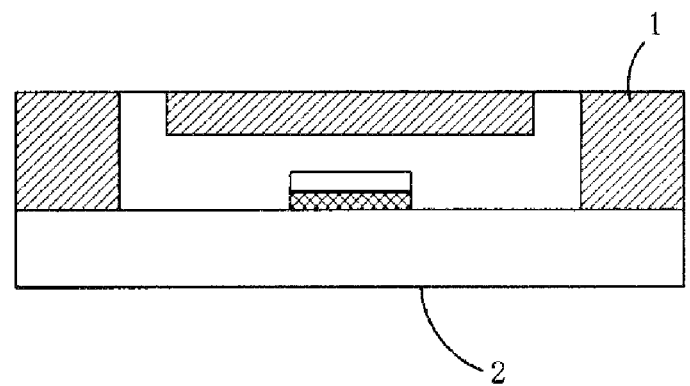

Next, according to the present embodiment, the following Process 4 and Process 5 is applied to the second microchip substrate 2 to which the above mentioned Processes 0 to 3 has been applied, as shown in FIG. 3. Accordingly, the metal foil film such as gold (Au) or the like is formed on the titanium oxide film formed on a portion of the second microchip substrate 2 made of glass.

(Process 4)

The second microchip substrate (glass molding) made of glass, to which the process 3 has been applied, is provided (installed) in a film forming (deposition) equipment that performs the film forming by way of the vapor deposition method or the sputtering method or the like. A metal thin film such as gold (Au) or the like is formed on the glass molding at the shielding member side.

(Process 5)

The shielding member is exfoliated from the second microchip substrate. As a result of the exfoliation, the Au film is, except for those formed on the titanium oxide film, removed from the second microchip substrate along with the shielding member.

In the Process 4, the metal thin film 4 is formed on the glass molding at the shielding member side, to which the process 3 has been applied.

As mentioned above, as a metal material for forming the metal thin film, gold, silver, copper, and aluminum may be used. Nevertheless, in general, the gold (Au) may be in particular used as a metal material that corresponds to the visible light or the near-infrared light and that is chemically stable. It should be noted that the metal material other than gold that has a similar efficacy as the gold may include, for example, platinum (Pt), and rhodium (Rh) and the like.

In the Process 5, with the shielding member being exfoliated from the second microchip substrate, the metal thin film such as Au or the like is, except for those formed on the titanium oxide film, removed from the second microchip substrate along with the shielding member.

Removing the shielding member can be performed by detaching a holder, which is not shown, and then detaching the shielding member from the second microchip substrate 2.

3. Process 6

Next, according to the present embodiment, the following Process 6 is applied to the second microchip substrate to which the above mentioned Processes 0 to 5 have been applied. Accordingly, a microchip is formed that is composed of the second microchip substrate and the first microchip substrate.

(Process 6)

The first microchip substrate is laminated onto the second microchip substrate to be joined together.

The joining of the microchip substrates can be performed by bonding the second microchip substrate 2 to the first microchip substrate 1, after the surface of the first microchip substrate 1 is irradiated with the vacuum ultraviolet light and the surface thereof is activated, as disclosed in, for example, the Patent Literature 5 (Japanese Patent Application Laid-open Publication No. 2006-187730A) and the Patent Literature 6 (Japanese Patent Publication No. 3714338B).

Figure 13A:
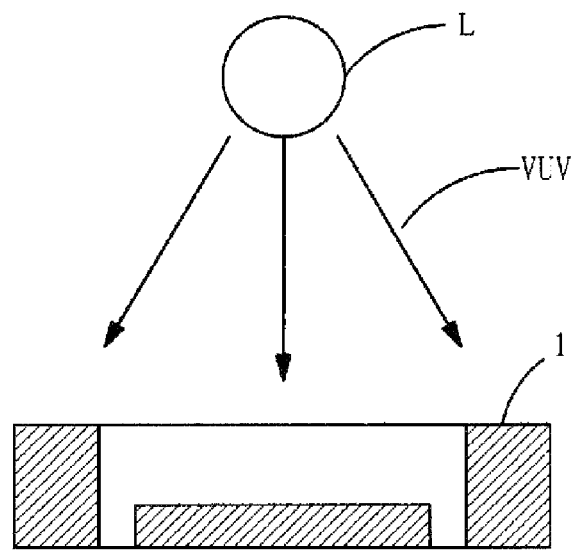
FIG. 13A is a view showing the light being irradiated onto a joining face of the first microchip substrate in the process for joining the first and second microchip substrates.

More particularly, as shown in FIG. 13A, the first microchip substrate 1 is irradiated with the light emitted from an excimer lamp and having a bright line at the wavelength of 172 nm so as to applying a reforming (modification) treatment (i.e., the oxidization treatment) onto the surface thereof.

Figure 13B:
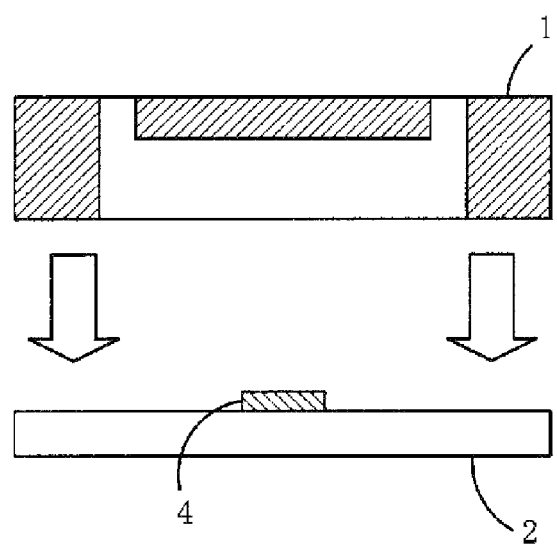
FIG. 13B is a view showing the process for joining the first and second microchip substrates.
Figure 13C:
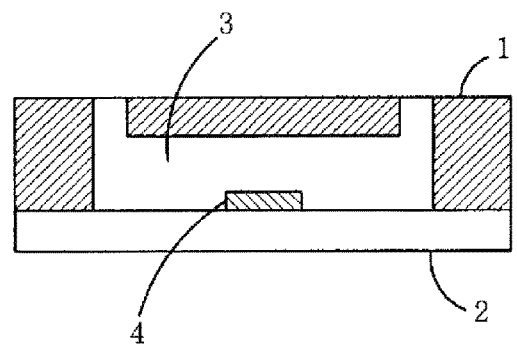
FIG. 13C is a view showing the configuration of the microchip obtained by the joining process of FIGS. 13A and 13B.

Subsequently, as shown in FIG. 13B, a side of the first microchip substrate 1 to which the reforming treatment is applied is faced to a face of the second microchip substrate 2 on which the metal thin film 4 is applied, and both substrates are laminated, and adhered to be joined together. Accordingly, the microchip as shown in FIG. 13C can be obtained.

By forming the microchip for the SPR sensor as explained above, the following effect can be achieved.

(1) According to the microchip of the present embodiment, the titanium oxide film having the smaller extinction coefficient is employed as the buffer film for the metal thin film to be applied the second microchip substrate 2. Thus, the deviation in the film thickness of the buffer film is less likely to affect the SPR signals. As a result, the film thickness of the titanium oxide film is not required to accomplish the higher uniformity of approximately 1 nm as in the case of the titanium film.

(2) Also, the titanium oxide film has the hydrophilic surface and the better adhesiveness to the metal thin film such as gold or the like. Thus, it is useful as an adhesive layer for improving the adhesiveness between the second microchip substrate 2 of the glass substrate and the metal thin film 4. In other words, as the titanium oxide film formed according to the titanium oxide film of the present invention has the hydrophilic surface, when the gold film 4a is formed on thus formed titanium oxide by way of the vapor deposition method or the sputtering method, the binding state between the titanium oxide film and the gold film 4a becomes stronger. In addition, the thickness of the gold film 4a can become relatively uniform.

(3) As already explained referring to FIGS. 4 to 12, it is assumed that the titanium oxide film is formed on the second microchip substrate 2 according to the present embodiment by repeatedly performing (c-1) the oxidization of titanium, (c-2) the binding of the oxidized titanium to oxygen, and (c-3) the binding of the bound oxygen to the titanium. In other words, as the immersion time elapses, the film thickness of the titanium oxide on the base material becomes thicker. Thus, the film thickness of the titanium oxide film can be easily controlled by controlling the immersion time. In other words, the film thickness of the titanium oxide film can be controlled by washing the surface with water as in the Process 2 to stop the reaction for forming the titanium oxide film.

(4) Also, because the titanium oxide is formed without using the hydrolysis reaction, the solution temperature is not required to be set at the higher temperature than an ambient temperature.

(5) The titanium oxide film formed according to the present embodiment is grown in the covalent binding between oxygen on the glass surface and titanium ion. Thus, even if the film thickness of the titanium oxide formed is relatively thick, still the titanium oxide film is immobilized firmly on the glass surface, unlike in the case that the titanium oxide is immobilized on the glass surface by the physical absorption by use of the conventional Wet Process.

(6) Furthermore, during the processes forming the titanium oxide film, a burning process is not required that heats the titanium oxide up to several hundred degree Celsius for crystallizing the titanium oxide on the base material. Thus, the granulation (particles) of the titanium oxide due to the heating process is not likely to occur. For this reason, any defect can be avoided which may be caused due to the titanium oxide film being unintentionally exposed from the metal thin film 4 such as the gold film 4a or the like.

4. Specific (Working) Examples of the Present Embodiments

Hereinafter, specific (working) examples of the present embodiment will be described in detail. Nevertheless, the present invention is not limited to the following examples, and can be embodied by adding appropriate modification within the scope of the purpose of the present invention. It should be noted that, in a part of which description may be duplicated, the duplicated description may be appropriately omitted, but it is not to intend to limit the scope of the present invention.

Hereinafter, the working examples of the present embodiment will be described below, in turn, first (a) the Process 0 in which the shielding member having the aperture of which dimension corresponds to a location of the metal thin film 4 being provided on the second microchip substrate 2 (glass molding), and then a surface of the glass molding at the shielding member side is irradiated with the ultraviolet light to activate the surface of the molding; then (b) the Processes 1 to 3 in which the base material to which surface finishing applied in the Process 0 is immersed in the mixed solution of titanium chloride aqueous solution and sodium nitrite aqueous solution that is nitrite ion contained aqueous solution, the base material is pulled out and washed after the prescribed time elapses, and the base material after the washing is dried (air dried) at the ambient temperature.

[Process 0]

In the Process 0, as shown in FIG. 2, the shielding member 5 is provided that has an aperture 5a on the surface of the glass molding (i.e., the base material W), and a surface of the glass molding at the shielding member side is irradiated with the ultraviolet light.

The above mentioned shielding member 5 is, for example, a stencil having the aperture 5a composed of, for example, silicone, or stainless steel. The shielding member 5 is arranged and fixed on one face of the second microchip substrate 2 with a holder or the like, which is not shown.

Then, by irradiating the surface of the glass molding (the base material W) at the shielding member side with ultraviolet light, the surface is activated.

As the light source L, for example, the excimer lamp emitting the vacuum ultraviolet light with the central wavelength of 172 nm can be employed.

Figure 14:
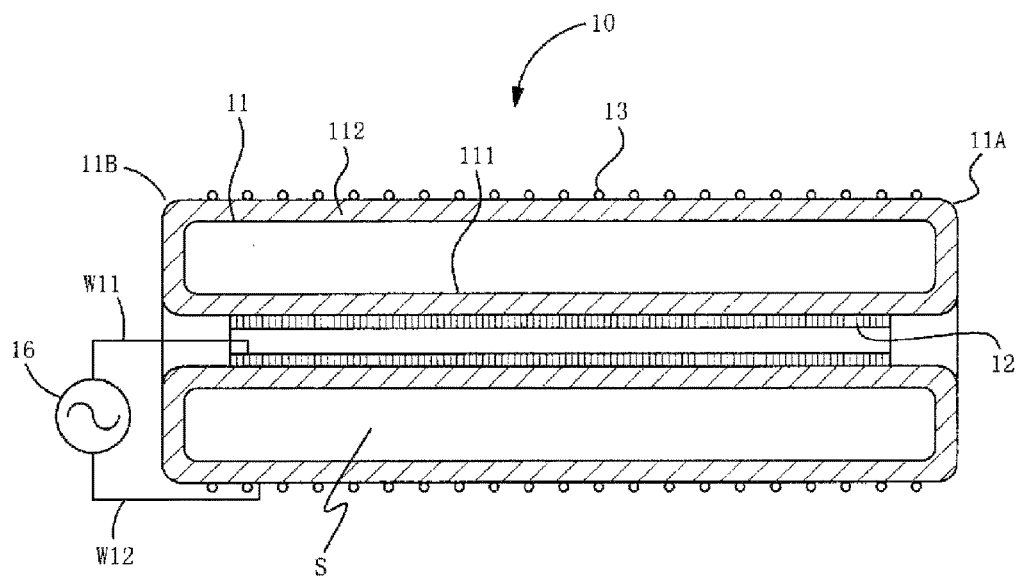
FIG. 14 shows an exemplary configuration of an excimer lamp.

FIG. 14 is a view showing an exemplary configuration of the excimer lamp. The excimer lamp has a tubular structure, and FIG. 14 shows a sectional view taken from a plane containing the tube axis. The excimer lamp 10 has a bulb (arc tube) 11 with a substantially double tube structure in which an inner tube 111 and an outer tube 112 are approximately coaxially arranged. A discharge space S with a cylindrical shape is formed inside the bulb 11 with both ends 11A, 11B of the bulb 11 being sealed. A noble gas such as xenon, argon, krypton or the like is enclosed in the discharge space S. The bulb 11 is made of quartz glass. An inner electrode 12 is disposed on an inner peripheral surface of the inner tube 111, and an outer electrode 13 with a reticular (net) shape is disposed on an outer peripheral surface of the outer tube 112. As such, those electrode 12, 13 are supposed to be arranged with the discharge space S intervening. The electrodes 12, 13 are connected to the power supply 16 through a lead wires W11, W12. When high frequency voltage is applied from the power supply 16, discharge (so called dielectric barrier discharge) is formed between the electrodes 12, 13 with dielectric substances (111, 112) intervening. In the case of xenon gas, the vacuum ultraviolet light with the central wavelength of 172 nm is generated and emitted to the exterior.

Figure 15:
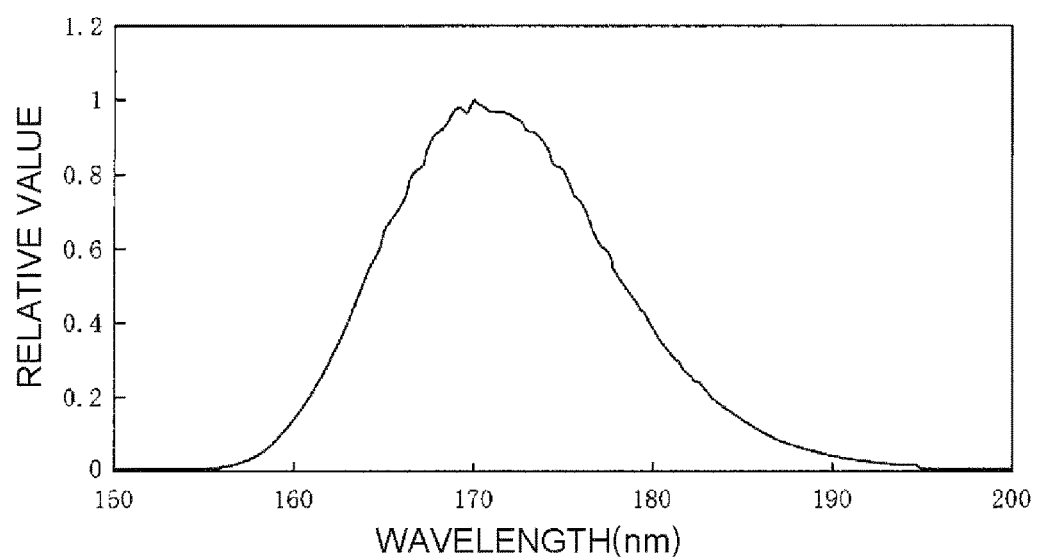
FIG. 15 is a view showing a distribution of the emission wavelength of the excimer lamp.

FIG. 15 shows an exemplary distribution of an emission wavelength (radiation wavelength) when the excimer lamp 10 shown in FIG. 14 is lighted with the frequency of 20 KHz and the bulb wall loading of 0.1 W/cm$^2$. The horizontal axis shows the emission wavelength, and the vertical axis shows relative values with respect to the light intensity of the light with the wavelength of 170 nm.

Figure 16:
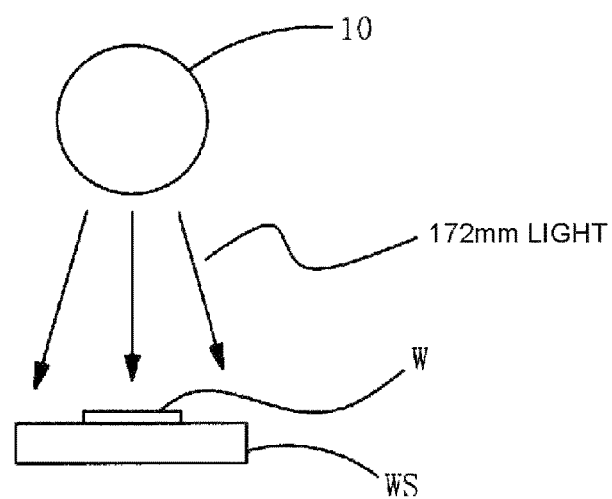
FIG. 16 is a schematic diagram showing an experimental system for irradiating the vacuum ultraviolet light onto the base material from the excimer lamp.

FIG. 16 is a schematic view of the experimental system. As shown in FIG. 16, the base material W on a work stage WS has been irradiated with the vacuum ultraviolet light from the excimer lamp 10. The excimer lamp 10 emitting the vacuum ultraviolet light with the central wavelength of 172 nm as mentioned above is employed, and the irradiance (radiation illuminance) on a surface of the specimen was 20 mW/cm$^2$.

The specimen is a molding molded with silicate glass, and is a square substrate having the dimension of 10 mm in thickness, 100 mm in height, and 100 mm in width.

Figure 17:
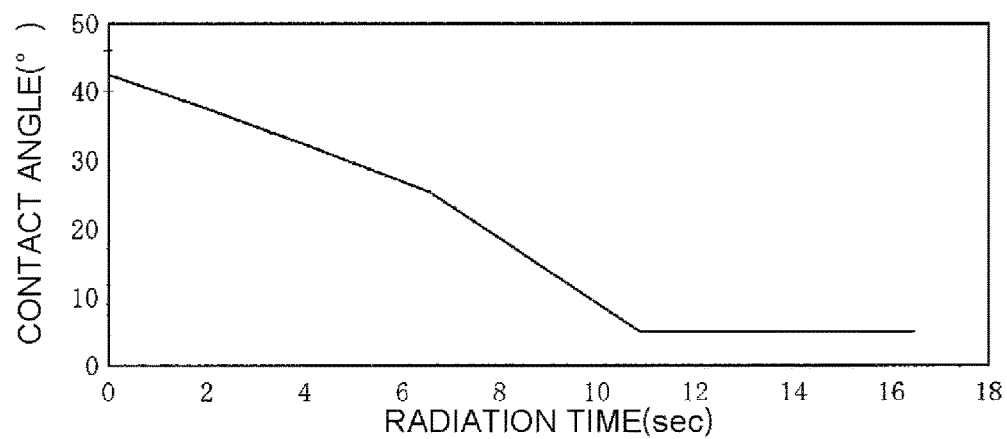
FIG. 17 is a view showing the wetting property (wettability) being improved by irradiation the ultraviolet light onto the glass.

FIG. 17 is a view showing an exemplary state demonstrating improved wettability when the glass is irradiated with the ultraviolet light. In FIG. 17, the horizontal axis shows the ultraviolet light irradiation time (sec), and the vertical axis shows the contact angle of water with respect to the glass (degree). FIG. 17 demonstrates data when alkali-free glass is irradiated with the ultraviolet light of 172 nm from the standard output excimer lamp (10 mW/cm$^2$) at an irradiation distance of 2 mm.

As shown in FIG. 17, with the glass being irradiated with the ultraviolet light, the contact angle (degree) of water with respect to the glass becomes smaller so that the wettability is improved. The reason why the wettability is proved to be improved is assumed that irradiating the glass with the ultraviolet light allows the glass surface to be active so that the terminal of the activated surface becomes the hydroxyl group (OH group).

To summarize, in the glass compact surface treatment process during the Process 0 in which the surface of the glass molding is irradiated with the ultraviolet light (vacuum ultraviolet light), the surface thereof is activated and the terminal of the activated surface becomes the hydroxyl group (hydroxyl group terminated). As long as determined from the above mentioned data, during the Process 0, more particularly, it is assumed that the binding portion between metallic atom or the like on the surface and oxygen is cleaved (cleavage occurs) as the activation of the surface, hydrogen is introduced from moisture in the atmospheric air into the cleaved portion, and the terminal of the glass surface ultimately becomes the hydroxyl group (terminated).

[Process 1], [Process 2] and [Process 3]

Next, hereinafter the Process 1, the Process 2, and the Process 3 will be explained.

The Process 1 is the process that the base material of the glass compact having a surface irradiated with the ultraviolet light (vacuum ultraviolet light) in the Process 0 is immersed in the mixed solution of titanium chloride aqueous solution and nitrite ion contained aqueous solution. The Process 2 is the process that the base material is pulled out from the mixed solution after the prescribed time elapses, and the base material is then washed. The Process 3 is a process that the base material after the washing is air dried at an ambient temperature.

The base material employed is a molding molded with silicate glass, and is a squared substrate with 2 mm in thickness, 8 mm in height, and 8 mm in width.

The base material was irradiated with the vacuum ultraviolet light from an excimer lamp emitting the vacuum ultraviolet light with the central wavelength of 172 nm for 1 to 2 minutes. The irradiance (radiant illumination) was equal to or less than 4 to 5 mW/cm$^2$.

Subsequently, during the Process 1, the Process 2, and the Process 3, the above mentioned base material was immersed in the mixed solution of titanium chloride (III) aqueous solution, with the concentration of titanium chloride (III) being 20% to 10 mM, and sodium nitrite aqueous solution, with the concentration of sodium nitrite being 0.1 M. Three kinds of mixed solution was employed that were regulated with hydrogen ion exponents of pH=7, pH=8.5, and pH=10, respectively, for the mixed solution in which the base material was immersed. It should be noted that to regulate to pH=8.5, calcium acetate was introduced into the mixed solution. Likewise, to regulate to pH=10, calcium acetate and sodium hydroxide were introduced into the mixed solution. After 30 minutes since the immersion started, the base material was pulled out from each of the mixed solution and then washed with purified water, and then air dried at an ambient temperature.

In order to observe the state of the surface of the specimen after the Process 1, the Process 2, and the Process 3, XPS-7000 type X-ray Electron Spectroscopic (XPS) Equipment, manufactured by Rigaku Co., Ltd., was used to perform the XPS measurement for the surface.

Figure 18:
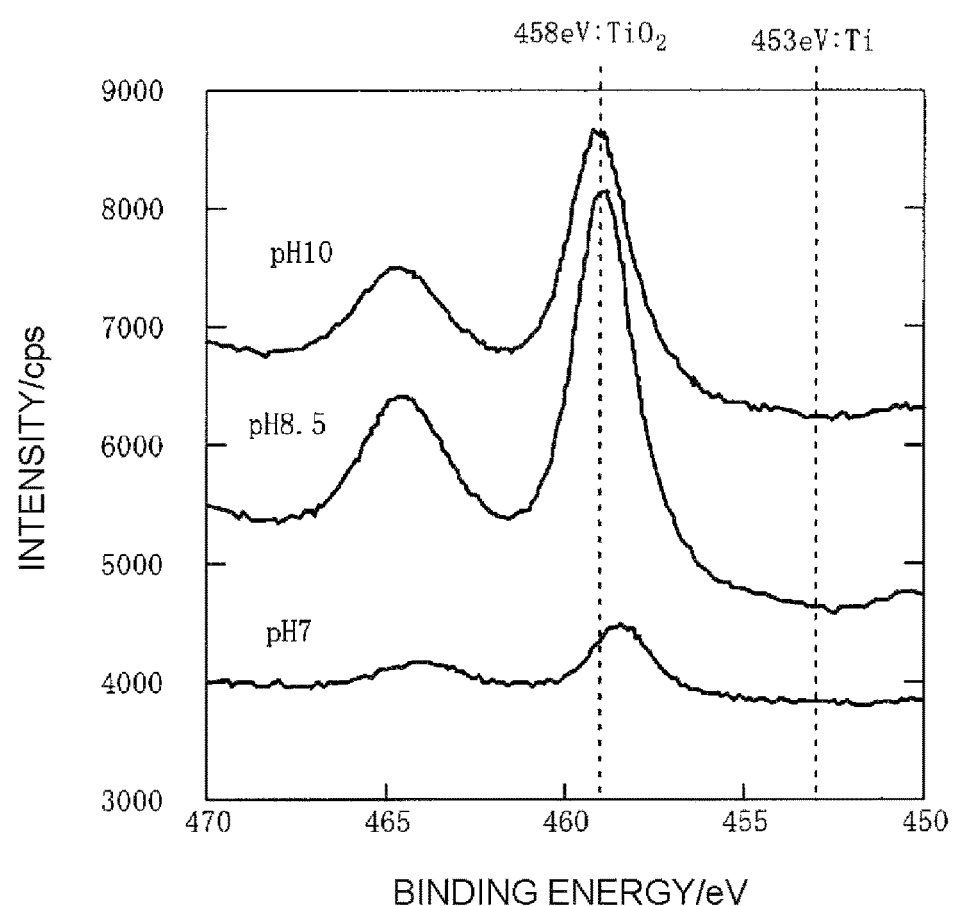
FIG. 18 is a view showing the XPS measurement results regarding the titanium oxide for the specimen to which the processes 0 to 3 of FIG. 2 are performed by use of three kinds of mixed solution.

FIG. 18 shows the result of the XPS measurement. In any of the base material immersed in the mixed solution with each pH value, although a peak in the vicinity of 453 eV, attribute to titanium (Ti), was not confirmed, a peak in the vicinity of 458 eV, attribute to titanium oxide ($TiO_2$) was confirmed.

In other words, by applying the treatment in the Process 1, the Process 2, and the Process 3, the titanium oxide film was formed on the surface of the molding made of silicate glass to which the treatment in the Process 0 was applied.

[Crystal Structure]

Glass (silicate glass) has an amorphous structure, and silicon and oxygen are irregularly arranged. As mentioned above, it is assumed that the crystal structure of the titanium oxide formed on the glass molding is defined by the location of oxygen existing on the surface of the glass molding. For this reason, it is considered that the arrangement of oxygen atoms exposed on the glass surface in the Process 0 (that is, the distribution of titanium ions to be bound to oxygen) is partially distributed such that the crystal structure of the growing titanium oxide film becomes the rutile type, while it is partially distributed such that the anatase type titanium oxide film is formed.

In other words, in the titanium oxide film formed on the surface of the glass molding with the amorphous structure, it is assumed that the rutile type titanium oxide and the anatase type titanium oxide are intermingled (mixed).

[Hydrophilic Property]

Subsequently, by applying the treatment in the Processes 0 to 3 using the above mentioned three kinds of mixed solution, a contact angle was measured on the surface of each molding on which the titanium oxide film was formed, with respect to the three kinds of glass moldings having the glass compact surfaces to which the titanium oxide films were applied. As a comparative example, a contact angle was measured on the surface of each molding before the titanium oxide film was formed on the surface. Water was employed as liquid for measuring the contact angle.

The contact angle of the glass molding surface before the titanium oxide was formed on the surface was approximately 60 degree. On the other hand, any of contact angles of the above mentioned three kinds of glass moldings on the surface on which the titanium oxide was formed was less than 10 degree. It is observed that when the titanium oxide is formed on the glass molding surface using the method for forming the titanium oxide film according to the present invention, the surface on which the titanium oxide was formed becomes the hydrophilic surface.

[Light Absorbance]

By applying the treatment in the Processes 0 to 3 using the above mentioned three kinds of mixed solution, the wavelength characteristic in the light absorbance was measured, for the three kinds of glass moldings having the glass molding surface to which the titanium oxide film were applied. As a comparative example, the wavelength characteristic of the light absorbance was also measured in the glass molding before the titanium oxide was formed on the surface. The Absorption Spectrophotometer (model U-3310), manufactured by Hitachi High Technologies Co., Ltd., was used for the measurement.

As a result, in the wavelength region of 300 to 700 nm, no variance was observed between the light absorption characteristic of the glass molding before the titanium oxide film was formed and the light absorption characteristic of the glass molding after the titanium oxide film was formed. Accordingly, it is turned out in the formed titanium oxide film, light absorption hardly occurs in the wavelength region of 300 to 700 nm.

In general, it is known that the titanium oxide demonstrates higher transparency with respect to the visible light region, when the particle size of the titanium oxide becomes of nano-sized. Thus, it is assumed that the film thickness of the titanium oxide formed on the glass molding surface this time is in the order of "nm".

It should be noted that as the immersing time in the mixed solution of titanium chloride aqueous solution and nitrite ion contained aqueous solution becomes longer, the film thickness of the titanium oxide film formed on the glass molding surface also becomes thicker. According to the experimental result conducted by the inventors of the present invention, it is turned out that the immersing time is preferably equal to or less than 30 minutes in order to maintain the transparency in the wavelength region of 300 to 700 nm.

The titanium oxide film formed on the glass molding (i.e., the second microchip substrate 2) according to the present embodiment is crystallized such that the rutile type and anatase type are mixed (intermingled). Thus, it make it possible to obtain stable adhesiveness.

In general, the rutile type titanium oxide film has higher transparency with respect to the light with the wavelength equal to or less than 300 nm compared to the anatase type titanium oxide film.

As the rutile type and the anatase type are mixed in the titanium oxide film according to the present embodiment, the titanium oxide film according to the present embodiment has the photocatalytic function with the anatase type titanium oxide film as well as the higher transparency with the rutile type titanium oxide film so that it has a smaller extinction coefficient.

Here, in the above mentioned examples, although the excimer lamp was used as the light source emitting the vacuum ultraviolet light, the present invention is not limited to those. For example, the noble (rare) gas fluorescent lamp may be used.

Figure 19A:
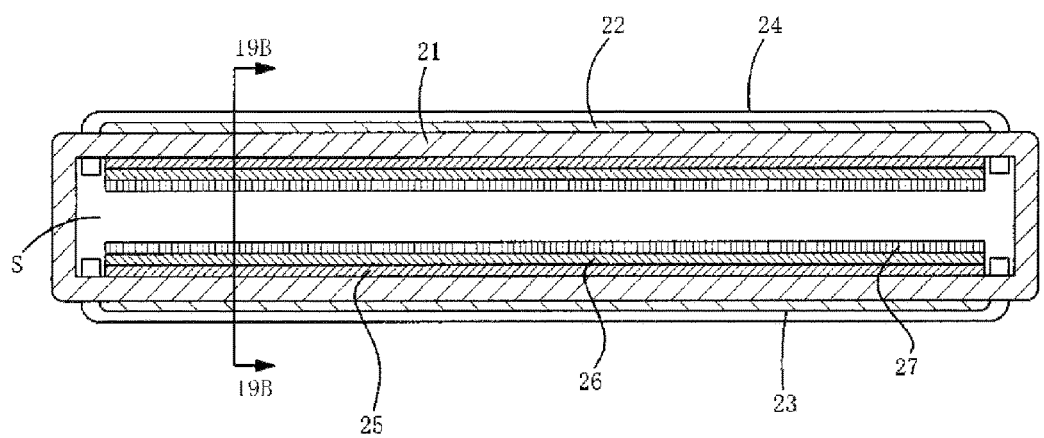
FIG. 19A is a side view showing another exemplary configuration of a noble (inert) gas fluorescent lamp.
Figure 19B:
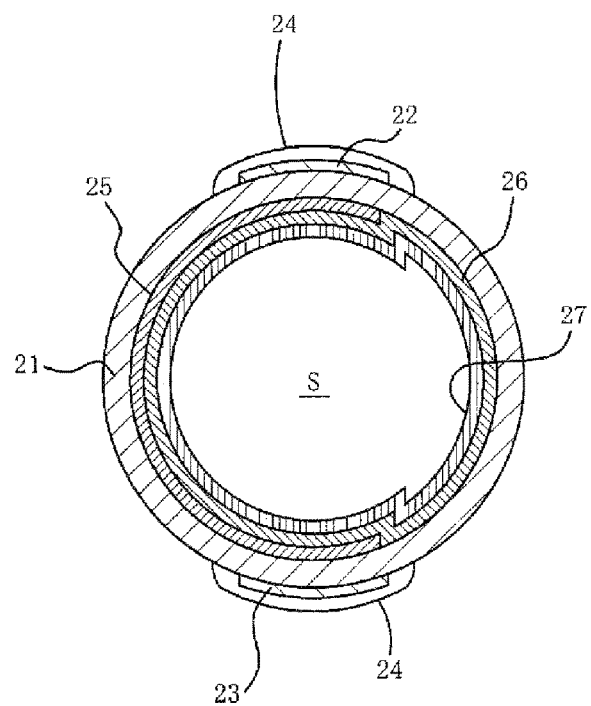
FIG. 19B is an enlarged sectional view taken from 19A-19A line of FIG. 19A.

FIGS. 19A and 19B shows another exemplary configuration of the noble gas fluorescent lamp. FIG. 19A is a cross sectional view taken by a plane including the tube axis, and FIG. 19B is a cross sectional view with 19B-19B line in FIG. 19A. In FIGS. 19A and 19B, a lamp 20 has a pair of electrodes 22, 23. The Electrodes 22, 23 is disposed on an outer peripheral surface of a bulb (arc tube) 21, and a protective film 24 is provided outside the electrodes 22, 23. An ultraviolet reflective film (coating) 25 is provided on an opposite inner surface with respect to a light emission direction side of an inner peripheral surface of the bulb 21 (as shown in FIG. 19B). A low softening point glass layer 26 is provided on its periphery (circumference), and a phosphor layer 27 is provided on an inner periphery surface of the low softening point glass layer 26. Other configuration is similar to those shown in FIG. 14. Likewise, gas enclosed in the discharge space S in the bulb 21 and a phosphor used for the phosphor layer 25 are also similar.

When high frequency voltage is applied to the electrodes 22, 23, dielectric barrier discharge is formed between the electrodes 22, 23 so that the ultraviolet light is generated, as mentioned above. It allows the phosphor to be excited, and the light emits from the phosphor layer. With the phosphor being appropriately selected, the ultraviolet light with the wavelength, for example, in the vicinity of 190 nm is emitted (generated) from the phosphor layer. This light is reflected with the ultraviolet reflective film (coating) 25 and then emitted outward from a portion of an aperture in which the ultraviolet reflective film 25 is not provided.

Also, when the irradiation region of the vacuum ultraviolet light on the molding surface is small, it is possible to employ a deuterium lamp emitting the light having the wavelength region including the vacuum ultraviolet light wavelength.

It should be noted that in the above mentioned examples, in the Process 0, the hydroxyl group (OH group) was introduced into the glass surface, and also the glass surface was irradiated by the light including the vacuum ultraviolet light with the wavelength equal to or less than 200 nm under an ambient atmosphere containing oxygen and moisture in order to remove contaminant such as an organic substance or the like, which may act as a reaction inhibition substance for forming the titanium oxide film. Nevertheless, other method can achieve the similar effect.

For example, the similar effect can be also achieved in the case that the glass is immersed in acidic solution such as hydrofluoric acid (HF), hydrogen peroxide water, or mixed acid (for example, mixed liquid of sulfuric acid and nitric acid in the volume ratio of 3:1) or the like, or alkaline solution such as sodium hydroxide aqueous solution or the like.

Furthermore, the similar effect can be also achieved in the case that the plasma discharge treatment (for example, atmospheric pressure plasma treatment) is applied to the glass surface under an atmosphere of the atmospheric pressure.

However, in the case that the immersing process in the acidic solution or the alkaline solution or the atmospheric pressure plasma treatment process is employed, the destructive action on the glass surface occurs, as well as the OH group introducing action on the glass surface and the removing action of the reaction inhibiting substance. Thus, the glass surface undergoes a damage so that the surface status becomes roughen. Accordingly, as the process to be employed in the Process 0, it is preferable to employ the process in which the glass surface is irradiated with the light including the vacuum ultraviolet light with the wavelength equal to or less than 200 nm.

Next hereinafter, (c) the Process 4 and (d) the Process 5 will be in turn explained. In (c) the Process 4, the second microchip substrate 2 (the glass molding) having the titanium oxide film in the aperture portion (section) of the shielding member 5 through the Process 0 to the Process 2, and the metal thin film 4 such as gold (Au) or the like is formed on the glass molding at the shield member side. In the Process 5, the shielding member 5 is exfoliated from the second microchip substrate 2, and the metal thin film 4 such as gold or the like is, except for those formed on the titanium oxide film, removed from the second microchip substrate 2 as well as the shielding member 5.

In the process forming the metal thin film 4 in the Process 4, as shown in FIG. 3, the gold film 4a was this time configured on the second microchip substrate 2 (the glass molding). The sputtering equipment was employed as a film forming equipment, and the gold film 4a was formed with the film thickness of 50 nm on the second microchip substrate 2.

In the process 5, the shielding member 5 made of the stencil is removed (detached) from the second microchip substrate 2 by, for example, detaching the holder, which is not shown.

Lastly, (e) the Process 6 in which the first microchip substrate 1 is laminated on the second microchip substrate 2 and both are joined together will be explained below.

Here, an exemplary joining procedure will be explained below in the case that the material of the first microchip substrate 1 is polydimethylsiloxane (PDMS), and the second microchip substrate 2 is the glass molding.

(a) First, with the configuration shown in FIG. 13A, a joining surface (to be joined) of the first microchip substrate 1 was irradiated with the light emitted from an excimer lamp with the central wavelength of 172 nm. The distance between an irradiation (irradiated) surface of the first microchip substrate 1 and a lower surface of the lamp is 3 mm. the irradiance (radiation illuminance) on the surface of the first microchip substrate 1 was 10 mW/cm$^2$, and the irradiation time was 120 seconds.

(b) Next, the light irradiated side of the first microchip substrate 1 is faced to the surface of the second microchip substrate 2 on which the metal thin film 4 is applied, and both substrates are laminated to be adhered each other.

(c) Subsequently, the laminated first and second microchip substrates 1, 2 were pressurized under the pressure of 1 kg/cm$^2$. The pressurizing time was 10 seconds, and after then the pressurized status was released.

(d) After then, the laminated first and second microchip substrates 1, 2 were placed on a heating stage, which is not shown and was preheated at 150 degree Celsius. After 5 seconds elapsed, the laminated first and second microchip substrates 1, 2 was pulled out from the heating stage.

By performing the above mentioned procedure, the microchip as shown in FIG. 13C was obtained.

Figure 20:
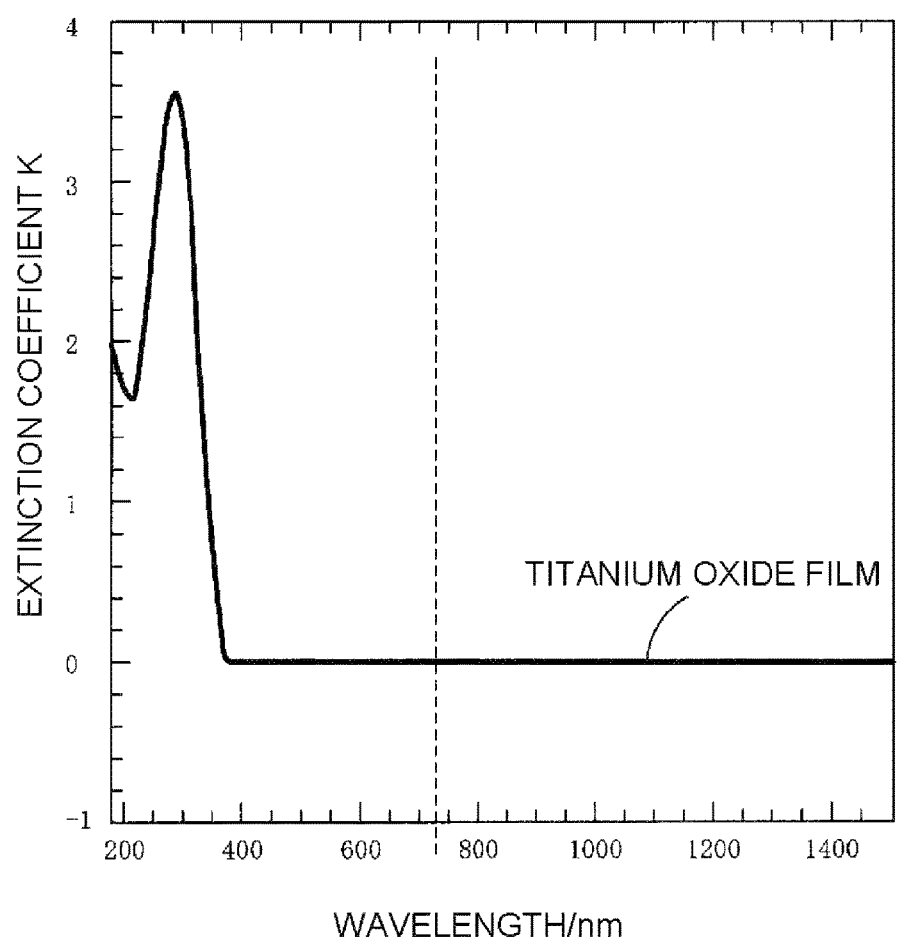
FIG. 20 is a view showing one example of the extinction coefficient with respect to the incident light wavelength of the titanium film and the titanium oxide film.

Next, FIG. 20 is a graph showing the extinction coefficient of the titanium oxide with respect to the incident light wavelength. In FIG. 20, the horizontal axis shown the wavelength (nm), and the vertical axis show the extinction coefficient. As apparent from the graph, the extinction coefficient of the titanium oxide is 0 at the wavelength of 670 nm. For this reason, in the case that the titanium oxide film is the buffer film, the film thickness of the titanium oxide is not likely to affect the SPR signals.

Taking the above mentioned observation into consideration, the SPR signal sensitivities were obtained by the simulation and then compared each other in the case that the buffer film of the metal thin film is the conventional titanium film and in the case that the buffer film of the metal thin film is the titanium oxide film according to the present invention.

The simulation condition was set such that the incident light wavelength is 670 nm, the metal thin film 4 has the film thickness of 40 to 50 nm, and the SPR resonance angle 71 of degrees (fixed angle condition).

Figure 21:
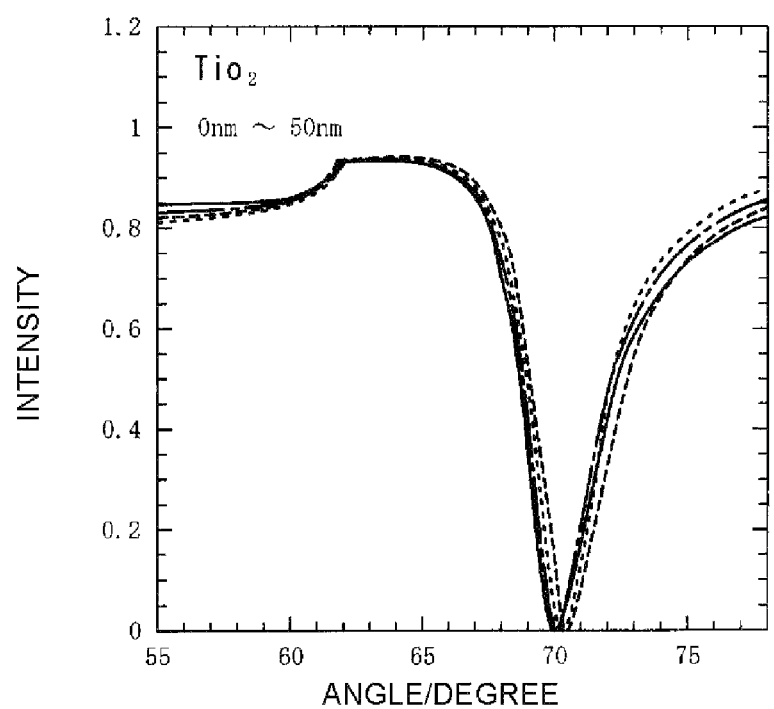
FIG. 21 is a view showing one example of a variance in the SPR signals with respect to the film thickness of the titanium oxide film.
Figure 22:
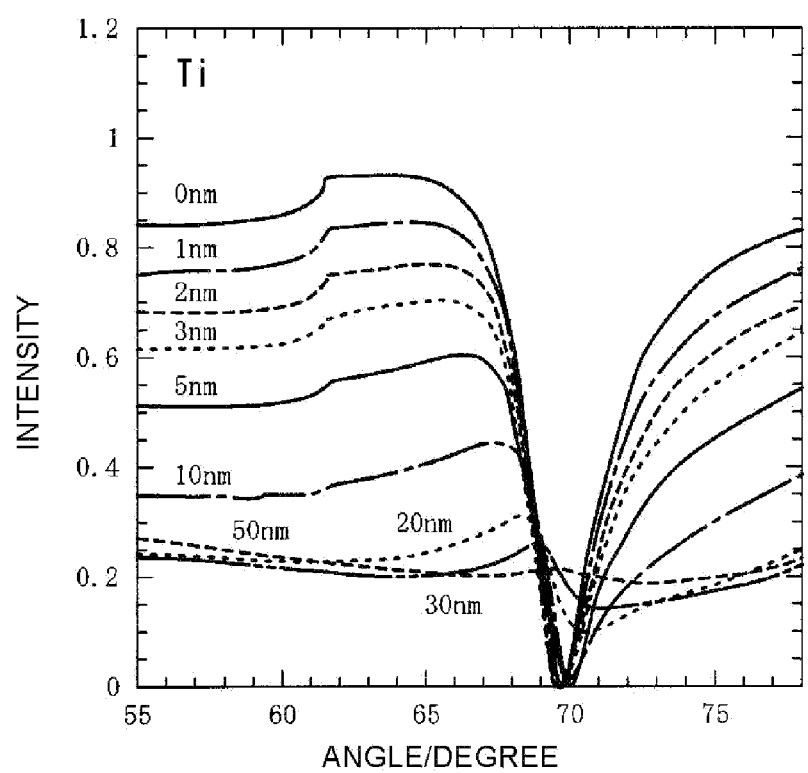
FIG. 22 is a view showing one example of a variance in the SPR signals with respect to the film thickness of the titanium film.
Figure 23:
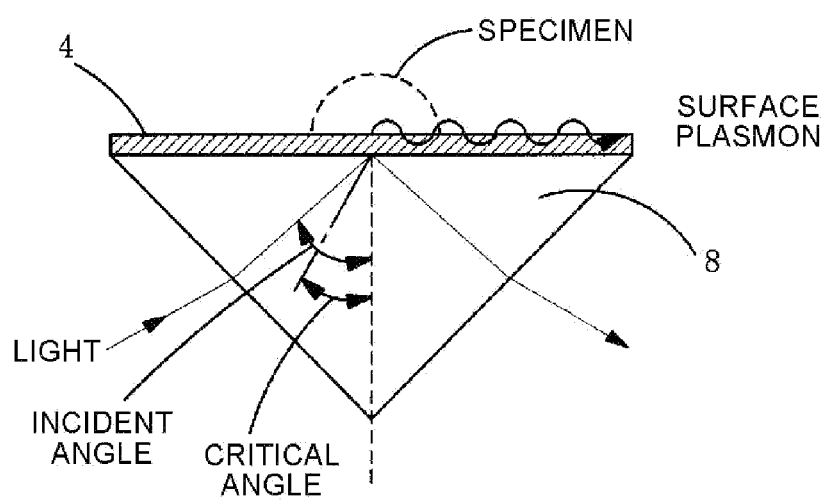
FIG. 23 is a schematic diagram showing a SPR sensor.
Figure 24:
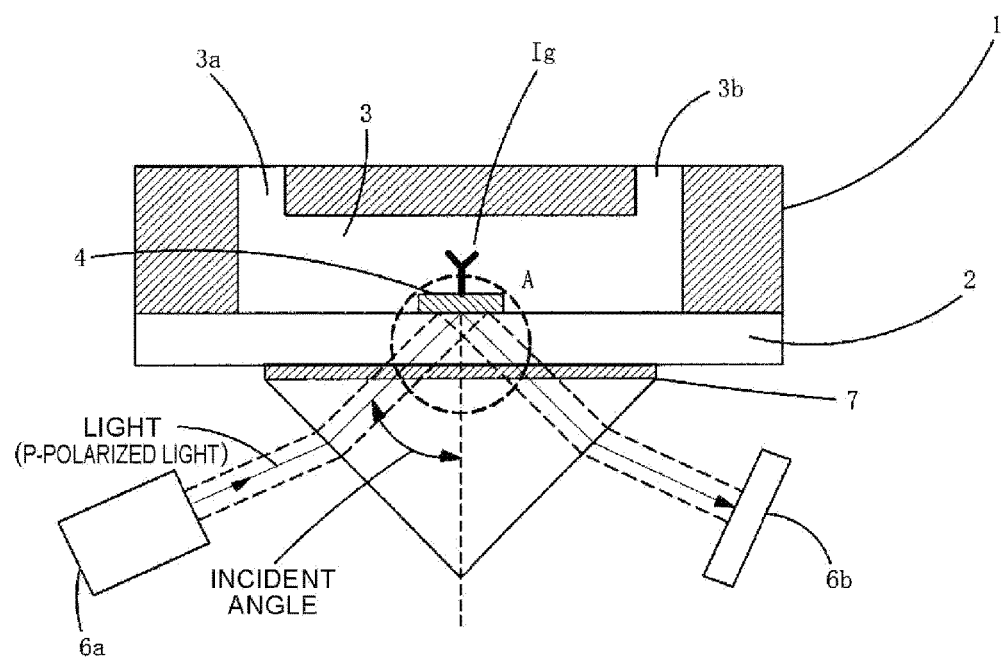
FIG. 24 is a view showing an exemplary configuration of the microchip and the SPR sensor employing the microchip.
Figure 25:
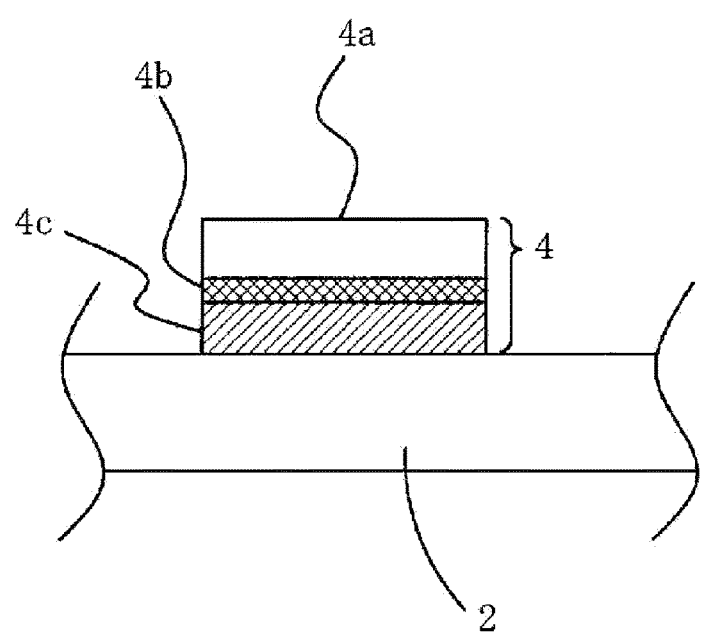
FIG. 25 is a view showing an exemplary configuration of the metal thin film having the titanium film.
Figure 26:
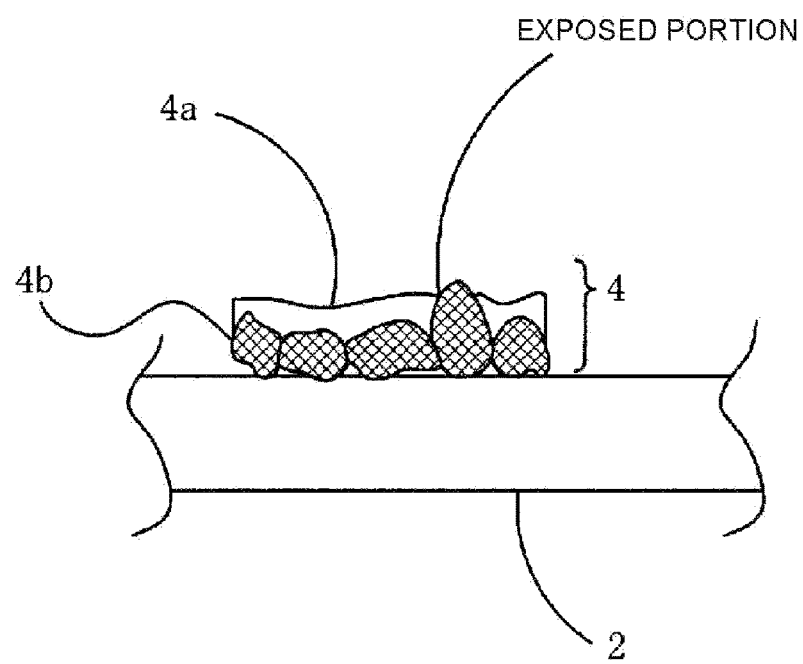
FIG. 26 is a schematic diagram showing a case in which the titanium oxide film immobilized onto the surface of the glass base material becomes in a shape of particles.

Then, within the rage of the film thickness of the titanium film or the titanium oxide film being 0 to 50 nm, it was observed how the SPR signals varied. FIG. 21 shows the case of the titanium oxide film, while the FIG. 22 show the case of the titanium film. In FIGS. 21 and 22, the horizontal axis shows the incident light angle, and the vertical axis shown the SPF signal intensity.

As apparent from FIG. 22, in the case of the titanium film, it is observed that the intensity of the reflected light of the light irradiated onto a rear face of the metal thin film 4 considerably (largely) varies depending on the film thickness within the range of the film thickness of 0 to 50 nm. In contrast, as apparent from FIG. 21, in the case of the titanium oxide film, it is observed that the intensity of the reflected of the light irradiated onto the rear face of the metal thin film 3 hardly differs depending on the film thickness with the rage of the film thickness of 0 to 50 nm.

As a result, it is turned out the titanium oxide film is preferable to be employed as the buffer film of the metal thin film 4 for the fixed angle type SPR sensor.

It should be noted that although particular embodiments have been explained above, the above mentioned embodiments are only for the illustrative purpose, and not intended to limit the scope of the present invention. The apparatus and the method described in the specification may be reduced to practice in various embodiments other than the above disclosed ones. Also, any omission, replacement, and modification may be appropriately made to the above mentioned embodiments without departing from the scope of the present invention. It should be noted that those embodiments with omission, replacement, and modification is also within the scope of what is claimed in the claims and the equivalents thereof so that those embodiments also fall into the technical scope of the present invention.

The present application is based on Japanese Patent Application No. 2013-117836 (filed on Jul. 4, 2013) and claims the priority based on the above Japanese Patent Application. All those disclosed in the above Japanese Patent Application and Japan Patent Application No. 2013-35578 (filed on Feb. 26, 2013) are hereby incorporated into the present application by reference.

REFERENCE SIGNS LIST

1 First Microchip Substrate
2 Second Microchip Substrate
3 Channel
3a Inlet Port
3b Outlet Port
4 Metal Thin Film
4a Gold Film
4b Titanium Oxide Film (Buffer Layer)
5 Shielding Member
5a Aperture
10 Excimer Lamp
11 Bulb (Arc Tube)
12 Internal Electrode 13 External Electrode
16 Power Supply
21 Bulb (Arc Tube)
22, 23 Electrodes
24 Protective Layer
25 Ultraviolet Reflective Film
26 Glass Layer
27 Fluorescent Layer
L Lamp
W Base Material
WS Work Stage

What is claimed is:

1. A method of forming a metal thin film in a microchip including a substrate made of glass on which the metal thin film is formed, and a channel formed in a space including the metal thin film, the method comprising:
   irradiating a surface of the substrate with light including vacuum ultraviolet light with a wavelength equal to or less than 200 nm under an ambient atmosphere containing oxygen and moisture;
   immersing the substrate in titanium ion solution and forming a titanium oxide film having a rutile type structure and an anatase type structure being mixed on a vacuum ultraviolet light irradiated face of the substrate; and
   depositing the metal thin film on the surface of the substrate on which the titanium oxide film is formed.

2. The method for forming a metal thin film in a microchip according to claim 1, wherein the metal thin film is composed of any of gold (Au), platinum (Pt), rhodium (Rh), palladium (Pd), or palladium-platinum alloy (Pd—Pt alloy).

* * * * *